US008165687B2

(12) United States Patent  
Cornejo Cruz et al.

(10) Patent No.: US 8,165,687 B2
(45) Date of Patent: Apr. 24, 2012

(54) SYSTEMS AND METHODS FOR DETECTING AND USING AN ELECTRICAL COCHLEAR RESPONSE ("ECR") IN ANALYZING OPERATION OF A COCHLEAR STIMULATION SYSTEM

(75) Inventors: Juan Manuel Cornejo Cruz, Del. Iztacalco (MX); Maria del Pilar Granados Trejo, Del. Iztacalco (MX)

(73) Assignee: Universidad Autonoma Metropolitana, Unidad Iztapalapa, Delegacion Iztapalapa (MX)

( * ) Notice: Subject to any disclaimer, the term of this patent is extended or adjusted under 35 U.S.C. 154(b) by 735 days.

(21) Appl. No.: 12/247,997

(22) Filed: Oct. 8, 2008

(65) Prior Publication Data

US 2009/0259277 A1      Oct. 15, 2009

Related U.S. Application Data

(63) Continuation-in-part of application No. 12/037,323, filed on Feb. 26, 2008, now Pat. No. 8,065,017.

(51) Int. Cl.
*A61N 1/05* (2006.01)
(52) U.S. Cl. ............................................. 607/57
(58) Field of Classification Search .............. 600/559; 607/55–57
See application file for complete search history.

(56) References Cited

U.S. PATENT DOCUMENTS

| | | | |
|---|---|---|---|
| 3,517,468 A * | 6/1970 | Woods | 52/79.1 |
| 4,400,590 A | 8/1983 | Michelson | |
| 5,626,629 A | 5/1997 | Faltys et al. | |
| 5,758,651 A | 6/1998 | Nygard et al. | |
| 5,999,856 A | 12/1999 | Kennedy | |
| 6,067,474 A | 5/2000 | Schulman et al. | |
| 6,157,861 A | 12/2000 | Faltys et al. | |
| 6,205,360 B1 | 3/2001 | Carter et al. | |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,428,484 B1 * | 8/2002 | Battmer et al. | 600/554 |
| 6,751,505 B1 | 6/2004 | Van Den Honert et al. | |
| 6,915,166 B1 | 7/2005 | Stecker et al. | |
| 2007/0204694 A1 | 9/2007 | Davis | |
| 2007/0293785 A1 | 12/2007 | Litvak | |

OTHER PUBLICATIONS

Firszt, Jill B. et al., Neurophysiology of Cochlear Implant Users I: Effects of Stimulus Current Level and Electrode Site on the Electrical ABR, MLR, and N1-P2 Response Ear & Hearing, 2002, pp. 502-515, 0196/0202/02/2306-0502/0, Lippincott Williams & Wilkins, USA.
Geier, Lisa L. et al., The Effects of Limiting the Number of Nucleus 22 Cochlear Implant Electrodes Programmed on Speech Perception, Ear and Hearing, 1992, pp. 340-348, vol. 13, No. 5, Williams & Wilkins, USA.

(Continued)

*Primary Examiner* — Scott Getzow
*Assistant Examiner* — Amanda Patton
(74) *Attorney, Agent, or Firm* — The Eclipse Group LLP

(57) ABSTRACT

Methods and systems for analyzing operation of a cochlear stimulation system. A sound stimulus signal is generated to excite the cochlear stimulation system to operate. During operation, the intracochlear electrodes generate signals into the auditory nerve system. The patient's nervous system's response may be measured as the Electrical Cochlear Response ("ECR"). The ECR can be detected and analyzed for fitting, calibration, performance evaluation and failure detection of the cochlear implant of the patient. Also example methods may be used to estimate the audiometric thresholds of the cochlear implant without the implanted patient's knowledge.

20 Claims, 18 Drawing Sheets

OTHER PUBLICATIONS

Gordon, Karen A. et al., Toward a Battery of Behavioral and Objective Measures to Achieve Optimal Cochlear Implant Stimulation Levels in Children, Ear & Hearing, 2004, pp. 447-463, 0196/0202/04/2505-0447/0, Lippincott Williams & Wilkins, USA.

Hughes, Michelle L. et al., A Longitudinal Study of Electrode Impedance, the Electrically Evoked Compound Action Potential, and Behavioral Measures in Nucleus 24 Cochlear Implant Users, Ear & Healing, 2001, pp. 471-486, 0196/0202/01/2206-0471/0, Lippincott Williams & Wilkins, USA.

Mahoney, Mary Jane et al., The User of Averaged Electrode Voltages to Assess the Funtion of Nucleus Internal Cochlear Implant Devices in Children, Ear & Healing, 1994, pp. 177-183, 0196/0202/94/1502-0177$3.00/0, Williams & Wilkins, USA.

PCT International Search Report and Written Opinion, International Application No. PCT/MX 08/00151 mailed Apr. 17, 2009.

* cited by examiner

SYSTEMS AND METHODS FOR DETECTING AND USING AN ELECTRICAL COCHLEAR RESPONSE ("ECR") IN ANALYZING OPERATION OF A COCHLEAR STIMULATION SYSTEM

FIELD OF THE INVENTION

The present invention relates to cochlear stimulation systems, and more particularly to methods and systems for obtaining and using an Electrical Cochlear Response ("ECR") in fitting, calibrating and evaluating operation of a cochlear stimulation system.

BACKGROUND OF THE INVENTION

Hearing impaired individuals typically suffer from a loss of hearing that falls in one of two general categories: conductive and sensorineural. Conductive hearing loss results from a failure in the mechanical chain in the external and middle ear that captures and drives the sound to the cochlea. Sensorineural hearing loss is due to the deficiency or damage in the cochlea, particularly of the hair cells located in the cochlea, which converts the sound to electrical signals that are transmitted by the auditory nerve to the part of the brain that creates the sensation of hearing.

Conductive hearing losses may be corrected, at least partially by medical or surgical procedures or by using conventional hearing aids to amplify the sound in order to increase its energy and patient be able to perceive sounds of the external word. Sensorineural hearing loss on the other hand may be corrected using a cochlear stimulation systems or, cochlear implant.

Cochlear stimulation systems operate by converting sound to electrical signals, which are applied to the residual auditory system through an intracochlear electrode array. The intracochlear electrode array provides electrical stimulation directly to the auditory nerve fibers to create a sound perception in the brain of a patient using the cochlear stimulation system.

A typical cochlear stimulation system includes an audio pickup, or input (for example, a microphone), an amplifier, a sound processing system, and a receiver/stimulator coupled to an intracochlear electrode array. The intracochlear electrode array and receiver/stimulator are typically part of an implanted portion of the system. The audio pickup, amplifier and sound processor are part of the external components of a cochlear stimulation system. The audio pickup is typically located on an earpiece having a connection to the sound processing system. The sound processing system also connects, wirelessly or via a wire, to a transmitter that is typically attached to the patient's head near the audio pickup earpiece. The transmitter is attached to the head at a location that is closest to a receiver connected to the implanted portion. The transmitter typically communicates with the receiver via a magnetic coupling. The implanted portion includes electronics that is coupled to the intracochlear electrodes or intracochlear electrode array. The intracochlear electrodes extend and terminate sequentially in a straight or spiraling line. The intracochlear electrodes are inserted into the cochlear tissue along the spiraling line that follows the spiral formed by the structure of the cochlea.

The intracochlear electrodes are assigned frequency bands in the auditory frequency range in order from highest frequency bands to lowest such that the highest frequency band electrodes are processed closest to the electronics in the implanted portion; the lowest frequency bands are processed closest to the end of the spiraling line, near the apex, i.e., the conical tip of the cochlea. The ordering of the frequency bands conforms to the functional structure of the cochlea, which is known to process incoming sound representing the highest frequencies at the base, i.e., beginning of the cochlea's spiral shape. Low frequencies are processed by the cochlear tissue extending further into the spiral shape in descending order, such that the lowest frequencies are processed near the apex.

During operation of the cochlear stimulation system, the audio pickup receives sound input and transmits the electrical signals to the sound processing system. The sound processing system multiplexes the signal by filtering the signal at a bank of bandpass filters connected in parallel. Each bandpass filter in the bank of bandpass filters corresponds to a different one of the intracochlear electrodes. The filtered signal is then assigned a current simulation level, which corresponds to a current of the signal to be output at the corresponding intracochlear electrode. The current stimulation level delivered to the cochlea by each intracochlear electrode is adjusted hopefully according patient's loudness sensation. Assigning frequency bands and setting a current level to each intracochlear electrode allows the cochlear stimulation system to represent incoming sound signal into an activation sequence to the intracochlear electrodes selected according to a stimulation strategy programmed into the sound processing system (described below). Basically, the current stimulation level is selected from a voltage level or some other indicator of the sound intensity of the input sound signal.

The filtered signal at the assigned current stimulation level are then de-multiplexed and sent to the transmitter. The transmitter transmits the de-multiplexed signal using a magnetic coupling to the receiver in the implanted portion. The signal is multiplexed to extract the filtered signals and each filtered signal is coupled to the individual intracochlear electrode corresponding to the filtered signal's bandwidth. The filtered signals excite the nerve fibers at the location of the corresponding intracochlear electrodes at a current level that is intended to correspond to the sound intensity level of the input sound. The patient senses the sound as the combination of frequencies corresponding to the intracochlear electrodes that generated the filtered signal and the combination of sound intensities corresponding to the current levels at each intracochlear electrode.

When a patient is provided with a cochlear stimulation system, a surgical procedure is performed to implant the components referred to above as being part of the implanted portion inside the ear. During the procedure, the intracochlear electrodes are inserted into the cochlea, and the receiver is implanted in an area of the ear that is opposite a space where the transmitter may be placed. The patient is also provided with the transmitter and audio input connected to the sound processing system.

A few weeks after the implant procedure, the cochlear stimulation system is also "fitted" for operation. The purpose of fitting the cochlear stimulation system is to adjust the range of current stimulation levels for each intracochlear electrode. The adjustment is necessary to ensure that the minimum current stimulation levels correspond to the lowest possible threshold sound intensity level that the patient can hear, and a maximum current stimulation level that will not result in pain or discomfort at high sound levels. That is, fitting permits a physician to determine the minimum and maximum psychophysical values of the stimulation current for each intracochlear electrode.

Cochlear stimulation systems are programmed to use a minimum and a maximum current value that hopefully match the hearing threshold level and most comfortable loudness level of the patient. The current stimulation level typically refers to a minimum and a maximum value, depending on the specific cochlear stimulation system, i.e. the electric current dynamic range. The full range of current stimulation levels corresponds to a range of sound pressure levels (in $dB_{HL}$) mapped according to the loudness perception of the patient. The sequence or order of activation of the intracochlear electrodes depends on the input sound features and stimulation strategy selected by the clinician, i.e., the code used to activate a subset of intracochlear electrodes according to the most important features of the incoming sound. The fitting of the implant involves generating a "MAP" of ranges of intracochlear electrode current stimulation levels, preferably meeting the particular needs of the patient. This means setting a threshold current stimulation level (or T level) and a maximum comfort level (or C level) for each electrode. Cochlear stimulation systems typically provide a procedure that allows a physician to set a T level and C level as well, to a desired value. It is assumed for purposes of this disclosure that the cochlear stimulation system being fitted provides such a facility, either using a manual mode that may be driven by software, or an automatic mode that permits downloading the T level from a computer or some other electronic device.

A variety of strategies exist for determining the T levels for each intracochlear electrode in a cochlear stimulation system. In some cases, the physician may choose to leave the cochlear stimulation system set to the T levels set by the manufacturer or use T levels in preconfigured maps of T levels to sound levels. The values of psychophysical parameters such as current stimulation levels are highly dependent on the physiology of the patient. Therefore, it is unlikely that predefined current stimulation levels would be suitable for many patients.

The physician may also use a subjective method where the physician stimulates the patient using a low level electrical current and increases the electric current level until the patient informs the physician that he can 'hear' the sound. The subjective method, however, cannot be implemented with children that cannot yet communicate. In fact, it is likely that any patient cannot communicate if they are experiencing the sense of hearing for the first time. Moreover, the patient is typically sedated from the implant procedure, which requires at least waiting until the patient can communicate in some way to perform the fitting.

Objective fitting methods have been developed for use with the patient sedated and possibly with children as well. Present objective fitting techniques measure physiological responses, such as the evoked compound action potential (ECAP), the middle ear reflex (MER), and the stapedius reflex (SR), to direct electrical stimulation of the intracochlear electrode. Cochlear stimulation systems that use objective fitting techniques typically include hardware and software components that provide the physician with control over the intensity of the electrical signals applied directly to the intracochlear electrodes. The electrical signals are typically biphasic, amplitude balanced pulses generated by an electrical signal source that is external to the cochlear stimulation system. The physiological responses are measured using either surface electrodes such as electroencephalographic ("EEG") electrodes, cochlear stimulation system intracochlear electrodes themselves or implanted electrodes, and the objective is to measure the response of the auditory nervous system to the applied electrical signals.

Known objective fitting techniques suffer from various drawbacks. First, such methods typically require the use of special fitting components that are part of the cochlear stimulation systems. The special fitting components are often proprietary apparatuses and methods designed for exclusive use with particular cochlear stimulation systems. Second, the techniques require generating electrical stimulation to the intracochlear electrodes that bypass the operation mode of the sound processing system of the cochlear stimulation system. Third, the techniques generally proceed by setting a T level for some of the intracochlear electrodes one at a time. This is time-consuming when setting the T level for all of the intracochlear electrodes and not very accurate when extrapolating from the T levels determined for a set of intracochlear electrodes to determine T levels for the rest. Fourth, the fitting does not factor in sound at all. The physiological response is a response to an electrical signal, and not sounds.

Known objective fitting techniques have been determined to result in a poor correlation between the threshold levels indicated by psychophysical measurements, for example, and T and C levels. In many cases, techniques that rely on direct stimulation to measure ECAP, MER, SR, and other physiological responses typically result in an overstimulation of the intracochlear electrodes during operation. These known objective techniques work by measuring responses to stimulation of single electrodes. This approach does not factor in that the physiological responses are different when processing actual sounds that involve the cumulative effect of multiple electrodes.

In view of the above, there is a need for improved systems and methods for performing objective fitting of cochlear stimulation systems.

SUMMARY OF THE INVENTION

In view of the above, improved systems and methods for fitting, calibrating, and/or otherwise analyzing operation of a cochlear stimulation system are provided. In one aspect of the invention, an example of a system is provided for analyzing operation of a cochlear stimulation system implanted in a patient. The system includes a sound generating system for generating a sound stimulus signal to elicit operation of the cochlear stimulation system. An electrical cochlear response ("ECR") detection system processes a plurality of electrical signal responses received from the patient using surface electrodes to detect an ECR waveform. The electrical signal responses being generated in response to the sound stimulus signal. The ECR waveform being indicative of operation of the cochlear stimulation system.

In another aspect of the invention, an example method is provided for analyzing operation of a cochlear stimulation system implanted in a patient. According to the example method, a sound stimulus signal having at least one selected frequency and sound intensity is generated. A plurality of electrical signal responses is generated in response to the sound stimulus signal. The electrical signal responses are processed as measured responses to the sound stimulus signal at generated frequencies and sound intensities. The measured responses are analyzed to determine if the electrical signal responses include an electrical cochlear response ("ECR") waveform. The ECR waveform being indicative of operation of the cochlear stimulation system.

Other systems, methods and features of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The above and other objects of this invention will become more readily apparent upon reading the following text and drawings, in which.

DETAILED DESCRIPTION OF THE PREFERRED EMBODIMENTS

I. Introduction

Figure 1A:
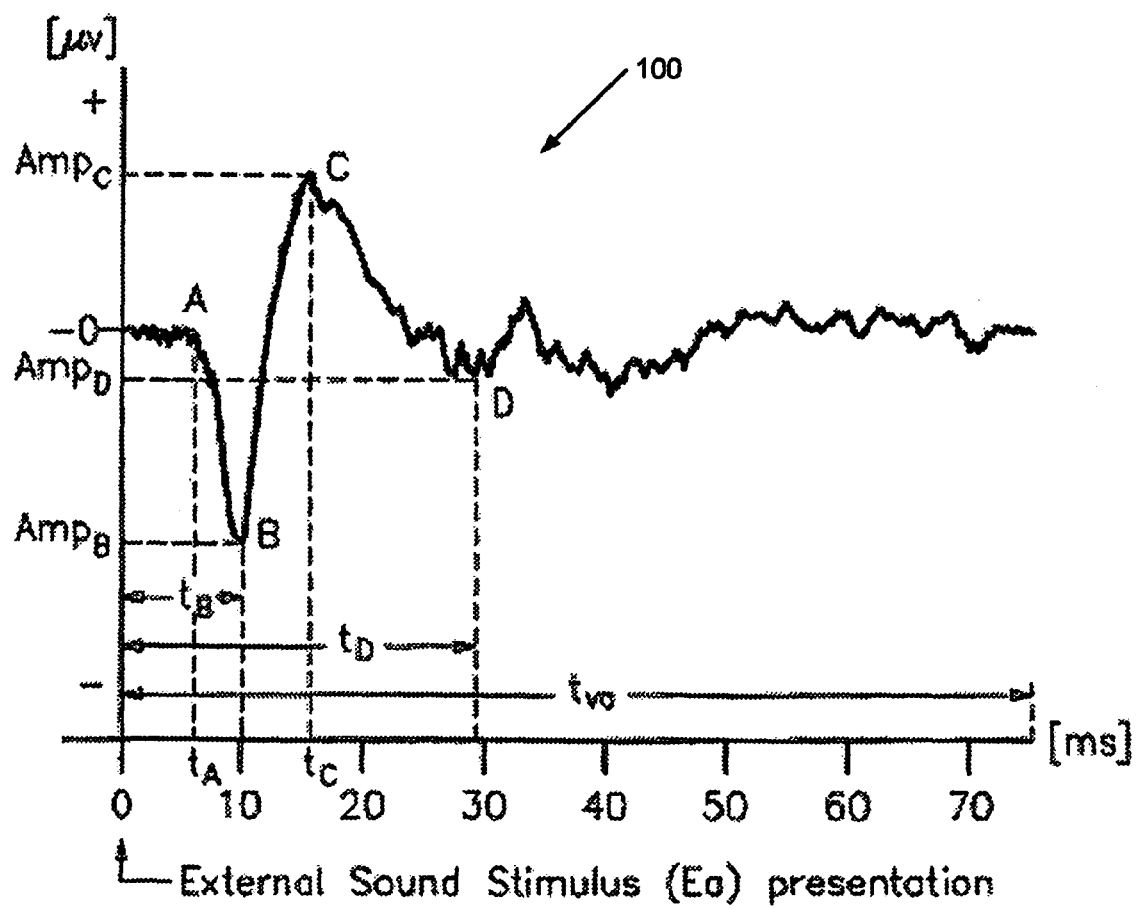
FIG. 1A is a graph depicting an example ECR waveform.

The following describes examples of systems and methods for fitting a cochlear stimulation system to a patient. The examples described below provide non-invasive objective techniques for fitting the cochlear stimulation system that may be performed with a sedated or sleeping patient, on adults or children. The examples also perform fitting techniques that involve adjusting the dynamic range of psychophysical levels in response to actual sound, and not to direct electrical stimulation of the intracochlear electrodes. The examples may also be implemented for use with any cochlear stimulation system that permits adjustment of psychophysical levels during fitting. Even cochlear stimulation systems that do not require fitting may make use of example systems and methods described below in performance evaluation, fault detection or audiometric threshold evaluation.

The examples below are described in the context of cochlear stimulation systems that are fitted by setting a T level (and if capable, a C level as well) in terms of a dynamic range of current stimulation levels. However, it is to be understood that example systems and methods may be implemented to perform fitting by setting any psychophysical parameter(s) according to sound levels. The examples are also described in the context of cochlear stimulation systems having an external, non-implanted component that contains a sound processor, and components for programming, or mapping, and for implementing a stimulation strategy. However, it is to be understood that the sound processor may be anywhere, even in the implanted component, and examples of the systems and methods described below may be used to provide fitting of such fully implanted cochlear stimulation systems.

The example systems and methods described may be used to perform a variety of functions. Such functions include:
1. Fitting—the setting of the dynamic range of current stimulation levels for each intracochlear electrode that is appropriate for the individual patient;
2. Calibrating—the setting of the dynamic range of current stimulation levels for each intracochlear electrode using a known T level for a given frequency value as an initial setting;
3. Performance Evaluation/Fault Detection—for assessing the operation of the cochlear stimulation system, or even for detecting faults in the implant procedure;
4. Audiometric Threshold Estimation—for assessing the implanted patient's hearing while using the cochlear stimulation system.

It is to be understood that the list of functions above is not an exhaustive list of functions that may be performed. These functions are just examples of the many functions available to physicians, clinicians or other professionals having patients that use a cochlear stimulation system and are able to analyze the patient's Electrical Cochlear Response ("ECR").

II. The Electrical Cochlear Response

The Electrical Cochlear Response ("ECR") is a measure of electrical activity generated by the residual cochlear tissue in response to an electrical stimulation that results when the cochlear stimulation system processes an external sound. The ECR is measured in response to an external sound having a known sound intensity and frequency. The ECR measurement is taken as a function of actual sound being processed by the sound processor components of the cochlear stimulation system being fitted. Because the ECR is measured using signals generated by the user's residual cochlear tissue and in response to actual sound being processed by the components of the cochlear stimulation system, the information obtained by using the ECR are tailored to the user's particular needs.

FIG. 1A is a graph depicting an example ECR waveform 100. The ECR waveform 100 is an electrical potential over a time period due to electrical current passing through an intracochlear electrode whenever a patient's cochlear stimulation system processes a sound. The ECR waveform 100 is characterized by parameters ("ECR parameters") determined from patterns and measurements that change in accordance with changes in sound intensity and frequency of the input sound. The time-variant, ECR waveform 100 may be picked up by using several electrodes used to pick up EEG activity ("EEG electrodes") strategically placed on the patient's head to receive the strongest possible nervous system responses to sound. During the detection of an ECR waveform 100, a sound having a known intensity and frequency is generated and processed by the cochlear stimulation system. As the sound is being processed, the patient's EEG signals are picked up at the EEG electrodes and stored. The EEG signals contain the ECR waveform 100 if the sound is being processed and therefore perceived by the patient. As such, the ECR waveform 100 includes electric potential contributions from auditory nerve fibers activity, cochlear nucleus and residual cochlear tissue in the intracochlear electrode vicinity.

The EEG signals contain other types of signals that may be much stronger than the ECR waveform 100. For example, signals arising from neuromuscular activity, or other types of nerve and/or brain activity, all of which may have stronger signals than the ECR waveform 100, may also be part of the EEG signals. The ECR waveform 100 may be "extracted" from the EEG signals by recording the EEG signals as multiple time segments of EEG signals picked up while the patient is subjected to a sound with a known and fixed intensity and frequency. The multiple time segments are then averaged to reduce the effect that electrical activity not associated with the sound has on the EEG signals. This process is described in more detail below with reference to FIG. 1B.

ECR waveforms 100 may be recorded for each frequency band to which an intracochlear electrode is assigned, and thus obtain an ECR for each electrode. The sound intensity is adjusted according to the function being performed.

The ECR waveforms 100 include ECR activity peaks having measurable properties that can be grouped as temporal (latency and time course), spatial (morphology, amplitude and phase) and frequency properties. The changes in these properties may be measured or detected as the sound intensity level, frequency, or current stimulation levels are varied.

An individual ECR waveform 100 may include a negative potential peak B sometimes followed by a positive potential peak C, and followed by a negative potential peak D. The waveform 100 levels out along a basal line to approximately a zero potential value. Amplitude and time relationship of these peaks are labeled on the ECR waveform 100 in FIG. 1A as $Amp_B$, $Amp_C$, $Amp_D$ and $t_B$, $t_C$, $t_D$ respectively. The ECR may be obtained when the sound processor in the cochlear stimulation system senses and processes an input sound. The EEG signals are then detected at the EEG electrodes and processed to obtain the ECR waveform 100.

In FIG. 1A, the Y-axis or amplitude is measured in micro volts ("µV") and the X-axis is the time window duration measured in milliseconds ("ms"). The ECR waveform 100 is characterized by the following:

1. Point A is the ECR waveform 100 starting point;
2. Peak B is the minimum negative peak following point A;
3. Peak C is the maximum positive peak following peak B;
4. Peak D is the minimum negative peak following peak C;
5. $t_A$ is the elapsed time from a starting point of an analysis window of time that contains the ECR waveform 100 to the ECR starting point A;
6. $t_B$ is the elapsed time from the starting point of the analysis window to the negative peak B;
7. $t_C$ is the elapsed time from the starting point of the analysis window to the positive peak C;
8. $t_D$ is the elapsed time from the starting point of the analysis window to the negative peak D;
9. $t_{va}$ is the analysis window;
10. $Amp_B$ is the peak B amplitude;
11. $Amp_C$ is the peak C amplitude; and
12. $Amp_D$ is the peak D amplitude.

The ECR waveform 100 characteristics listed above change in relatively predictable ways as the intensity and frequency of the input sound changes. These changes in the characteristics reflect the change in residual cochlear tissue behavior that occurs when the patient perceives the changing sound characteristics (intensity and frequency). By identifying the intensity at which the ECR waveform 100 forms, a clinician may identify the threshold level ("T level"). By identifying the intensity at which the ECR waveform 100 starts to become distorted, the clinician may identify the comfort level (C level). The ECR waveform 100 provides an objective method for determining the T and C levels.

Figure 1B:
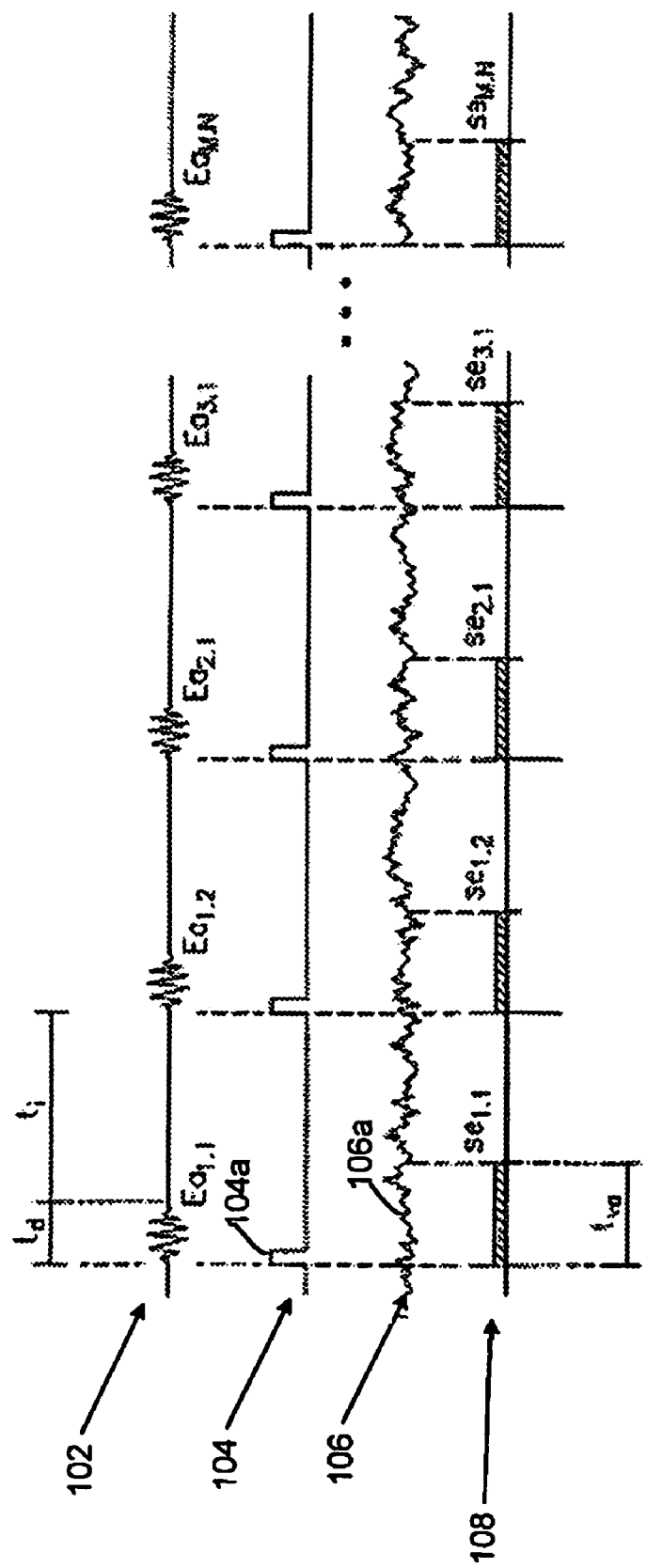
FIG. 1B shows a set of signals illustrating operation of a system for obtaining an ECR waveform.

FIG. 1B shows a set of signals illustrating operation of a system for obtaining an ECR waveform. FIG. 1B shows a set of signals illustrating operation of an example method for obtaining an ECR. FIG. 1B includes a first signal diagram 102, a second signal diagram 104, a third signal diagram 106, and a fourth signal diagram 108. The first signal diagram 102 is the input sound stimulus, $Ea_{M,N}$, generated in M epochs for each of N intracochlear electrodes. Each of the N electrodes corresponds to one of N frequency bands processed by the bandpass filters connected to each intracochlear electrode. Each intracochlear electrode is identified by number (electrode no. 1, electrode no. 2, etc.), which may be referred to as a channel number, between 1 and N, and assigned a corresponding frequency band. The signals in the first signal diagram 102 in FIG. 1B are:

$Ea_{1,1}$—a sound signal generated in epoch M=1 at a selected intensity and at a frequency=$f_c$, the center frequency of the frequency band processed by electrode no. 1.

$Ea_{1,2}$—a sound signal generated in epoch M=1 at a selected intensity and at a frequency=$f_c$, the center frequency of the frequency band processed by electrode no. 2.

$Ea_{2,1}$—a sound signal generated in epoch M=2 at a selected intensity and at a frequency=$f_c$, the center frequency of the frequency band processed by electrode no. 1.

$Ea_{3,1}$—a sound signal generated in epoch M=3 at a selected intensity and at a frequency=$f_c$, the center frequency of the frequency band processed by electrode no. 1.

The second signal diagram 104 shows a control signal 104a, which establishes the starting point of an analysis window that defines the time duration of an epoch. The control signal 104a in FIG. 1B is a pulse of any suitable pulse width that signals the start of: (1) a sound duration time, $t_d$, which is the time duration of the input sound; (2) an interval time, $t_i$, which is the interval time between two consecutive sound stimuli; and (3) the analysis window, $t_{va}$, which is the time duration of each epoch.

The third signal 106 in FIG. 1B is an EEG signal 106a picked up at the EEG electrodes. The EEG signal 106a is the signal that is detected and recorded for measurement. As the EEG signal 106a is recorded, it is stored in epochs. The fourth signal 108 shows the epochs as segments, $se_{M,N}$ having time duration of $t_{va}$ within the time interval $t_i$. When the epochs are recorded, the data is processed by averaging the epochs at a given electrode and at a given intensity (IS).

During operation, the input sound signal shown in the first signal diagram 102 is generated as a series of tones, or "pips," having the indicated characteristics. For example, a first pip, $Ea_{1,1}$, is generated for a duration $t_d$. Random sound, or no sound, is generated for a duration of $t_i-t_d$. The second pip, $Ea_{1,2}$, is generated for a duration of $t_d$ followed by no sound for $t_i-t_d$. The pips may be generated in any order, or randomly. In FIG. 1B, the first pip, $Ea_{1,1}$, is for the first epoch (M=1) corresponding to the data being collected for the electrode number 1. The next pip is for the first epoch corresponding to the data being collected for electrode number 2. The next pip in FIG. 1B is for the second epoch corresponding to the data being collected for electrode number 1. The next pip, $Ea_{3,1}$, is the third epoch corresponding to the data collected for the electrode number 1.

The pips are generated in whatever order is selected until the desired number of epochs, M, are collected for each electrode, the data is analyzed to determine if any ECR waveforms resulted from the input sound stimulus. Using the conventions established in the description above with reference to FIG. 1B, a measured response to the sound stimulus may be defined to the result of the averaging of the epochs collected at a given frequency and at a given intensity. Thus, a measured response for a given intracochlear electrode, j, may be expressed as SE $fc_{e(j)}$ in EQN. 1:

$$SEfc_{e(j)} = \frac{\sum_{K=1}^{M} se(j,k)}{M} @ IS: j = 1, 2, \ldots, N \qquad \text{EQN. 1}$$

The measured response, SE $fc_{e(j)}$, is a waveform formed by the average value of the signal levels in the EEG epochs at time increments within the analysis window. The data collected for a given intracochlear electrode, j, is analyzed, either visually, or using pattern recognition software.

In general, a visual inspection of the measured response may entail heuristically searching for ECR characteristics based on the following guidelines:

$t_A$ is typically less than about 10 ms.
$t_B$ is typically about 10±2 ms.
$t_C$ is typically about 15±2 ms.
$t_D$ is typically about 29±2 ms.

It is noted that these values may be typical for a test performed in sound field conditions with the speaker placed one meter away from the implanted patient. There may be differences in the values based on the individual patient, test conditions, and other factors. The values above are provided as an example and do not represent absolute parameters to which any results should conform. In addition, the clinician may inspect the values of amplitudes $Amp_B$, $Amp_C$, and/or the difference between the two ($Amp_C - Amp_B$). The clinician may determine desired minimum values of the amplitudes based, for example, on a model ECR waveform created by using historical data, such as measured responses that were deemed to be ECR waveforms for low threshold sound levels. The clinician compares the values of $Amp_B$, $Amp_C$, and/or $Amp_C - Amp_B$ with expected minimum values of each to determine whether the measured response is indeed an ECR waveform.

The heuristics described here for a visual inspection may also be implemented, for example, in a computer program designed to analyze the measured responses and determine if the responses are ECR waveforms.

When the analysis determines that an ECR waveform has been detected, the frequency of the pips generated to stimulate the ECR response is used to determine the intracochlear electrode involved in generating the ECR. The signal diagrams 102-108 in FIG. 1B illustrate a general method for obtaining an ECR. The information conveyed by the ECR varies according to the function being performed. For example, fitting involves setting the sound input to a desired low level for the particular patient and setting the frequency to select one of the intracochlear electrodes. The current stimulation level is then increased from a very low value until the ECR is obtained. The current stimulation level at which an ECR waveform was detected is then set as the T level. The C level may be determined experimentally by increasing the current stimulation level until the ECR waveform begins to show distortion. The C level may also be set to a percentage of T above the T level: C level=T level+% age of T level. The frequency is then adjusted to select another electrode and the current stimulation level is again adjusted to a low level to determine a T level (and C level) for the next electrode. The process continues until each electrode has been fitted.

In other functions, such as calibration of a cochlear stimulation system that has been operating, the sound intensity is set to a low inaudible level to begin with. The frequency is set to select an intracochlear electrode and the intensity is increased until an ECR is detected. This measured minimum sound level is compared to a desirable minimum sound level. If a meaningful difference exists between the desirable and the measured minimum sound levels, the current stimulation level is adjusted until an ECR waveform is detected for the desirable minimum sound level.

Figure 1C:
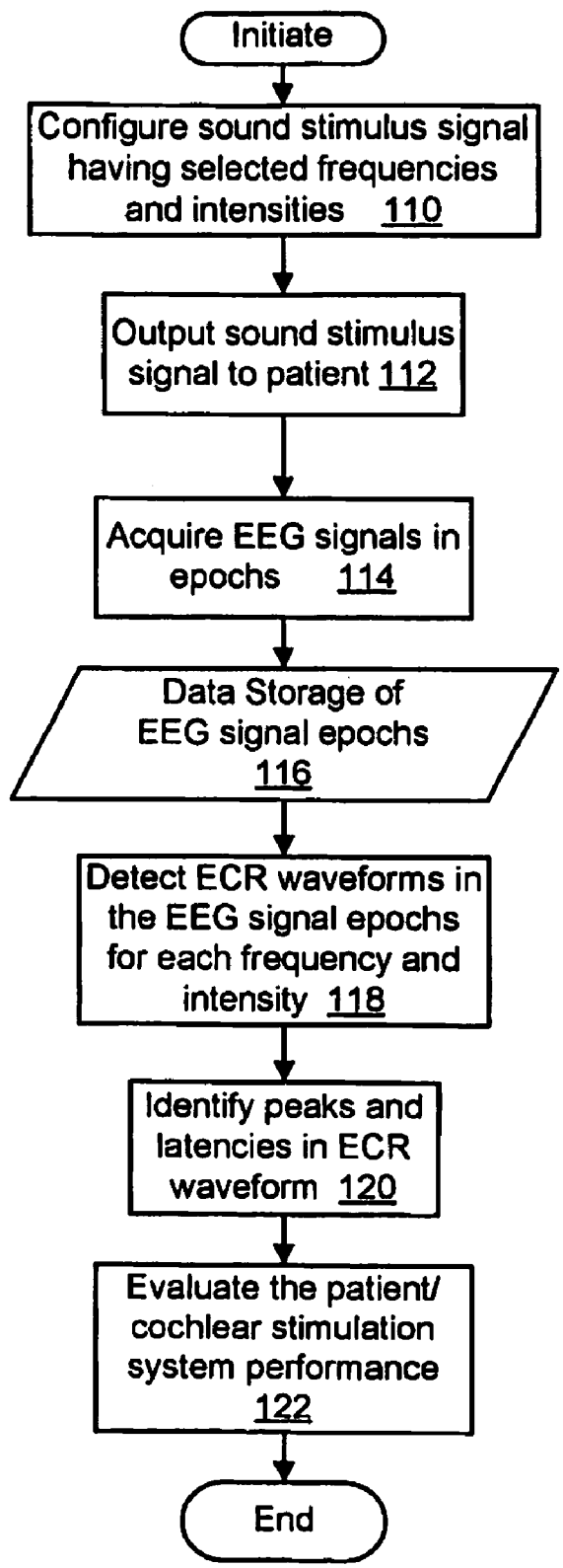
FIG. 1C is a flowchart illustrating an example method for obtaining an ECR waveform.

FIG. 1C is a flowchart illustrating an example method for obtaining an ECR waveform. The method illustrated in FIG. 1C may be performed once a patient has had a cochlear stimulation system implanted, and is connected to a selected set of EEG electrodes. In addition, the method illustrated in FIG. 1C may be used to perform virtually any function made possible by measuring the ECR. For example, the method in FIG. 1C may be part of a fitting process to set T and C levels in a newly implanted cochlear stimulation system. In the case of a fitting, the patient may be fitted while sedated or asleep when the cochlear stimulation system is turned on for the very first time a few weeks after implantation surgery. The method may also be part of a method for calibrating a cochlear stimulation system that has been in use. The method may also be part of a method for evaluating the performance or detecting fault in the system. Suitable systems for carrying out the method illustrated in FIG. 1C are described in more detail below with reference to FIGS. 2A-2C.

Once the cochlear stimulation system has been implanted, the system is initialized. Part of the initialization process may be to set the system with an initial set of T and C levels. Once initialized, a sound intensity level and frequency is selected as an initial set of test characteristics, as shown in Step 110. The sound with the selected frequency and intensity level is generated to be received as noise-free as possible by the sound pickup on the cochlear stimulation system as shown at Step 112. At Step 114, the epochs of EEG signal are acquired and stored in memory in a computer that may be connected to the EEG device to receive data. The epochs are keyed or indexed or otherwise organized to correspond to a given electrode (and therefore frequency band), and at the selected intensity level. The data organization may depend on the function being performed. If the patient is being fitted, Step 114 may be performed such that epochs are acquired at the selected frequency and desired low threshold intensity level an ECR is detected. The frequency is varied to fit each intracochlear electrode.

Step 116 is the storing step in which the epochs are stored in memory as described. Once the desired number of epochs has been collected, the data is analyzed at Step 118 to detect the ECR as described above with reference to FIG. 1B. Step 120 performs peak detection and measurement as part of a pattern recognition algorithm that may be applied to the epoch data. At step 122, the T level may be automatically set by software control. Step 120 may also be performed by displaying the ECR waveforms as a function of either intensity, frequency or both. The clinician may then decide on the basis of the ECR waveforms, which indicates a T level and which indicates a C level. Step 122 would then involve setting the T and C levels manually (or using the assistance of a computer) according to the specifications of the specific cochlear stimulation system.

In general, for the process of fitting the system, the intensity is set to a low threshold level, and the current stimulation level is increased until the epoch data indicates that it contains an ECR waveform. When an ECR waveform can be discerned, the clinician may note the frequency to identify the electrode and determine the current stimulation level being generated for the desired low threshold sound intensity level. The determined current stimulation level may then be set as the T level for the given electrode. In some cases, the clinician may also elect to specifically set the C level (comfort level) to set a maximum level for loudness. The clinician may determine the C level by increasing the intensity until the ECR waveform becomes distorted. The next lower level of intensity that produced an un-distorted ECR waveform may be selected for determining the C level.

III. Example Systems for Fitting a Cochlear Stimulation System

Figure 2A:
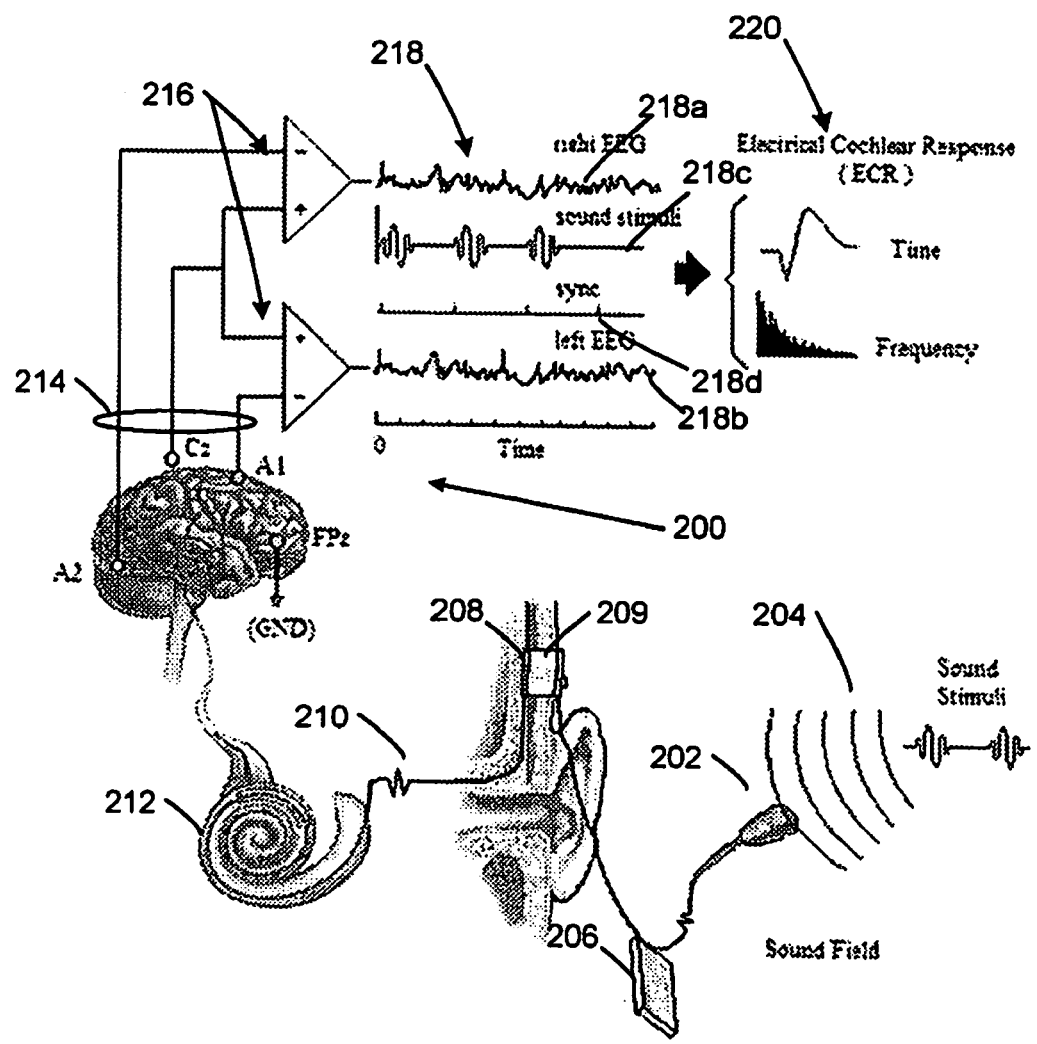
FIG. 2A is a schematic diagram depicting operation of an example system for obtaining an ECR and for fitting the cochlear stimulation system for use by the user.

FIG. 2A is a schematic diagram depicting operation of an example system 200 for obtaining an ECR and for fitting a cochlear stimulation system for use by the user. The system 200 in FIG. 2A is described in the context of fitting the user with a cochlear stimulation system, which includes a sound pickup 202 (such as a microphone, or other auditory signal input device), a sound processor 206, an implanted component 208, a transmitter 209, a signal-carrying lead 210 and an intracochlear electrode array 212. The system 200 for obtaining ECR includes a plurality of EEG electrodes (or, scalp electrodes), an EEG acquisition device 216 to output EEG signals, an ECR waveform processor 218, and a user interface 220.

FIG. 2A illustrates operation of the system 200 beginning with the generation of a sound stimulus 204 to be received by the sound pickup 202. The sound pickup communicates the electrical signals representing the sound to the sound processor 206, which processes the sound by de-multiplexing the electrical signals according to the frequency bands defining the bandpass filters in the sound processor 206, and by selecting the current stimulation level appropriate for the intensity of the sound. The signal is then communicated to the transmitter 209, which transmits the sound signal to a receiver in the implanted part 208. The implanted portion 208 includes electronics for multiplexing the signal to couple signals to the appropriate intracochlear electrode according to the frequencies of the multiplexed signal. The signals are carried over the signal-carrying lead 210 to the intracochlear electrode array 212.

As shown in FIG. 2A, the cochlear stimulation system operates as intended by processing the sound generated at the sound input 202. The characteristics of the sound may be controlled by, for example, controlling the intensity of the sound as well as the frequency of the sound. During operation of the cochlear stimulation system, the EEG acquisition device 216 pickups up EEG signals from the EEG electrodes 214. The EEG electrodes 214 include four electrodes. In an example implementation, the four EEG electrodes may include electrodes identified as $A_1, A_2, Cz$, and $FP_z$ according to a known convention for identifying EEG electrodes.

The EEG electrodes 214 may be placed on any part of the body from which the strongest possible EEG signals may be picked up. In general, the locations of the EEG electrodes 214 will be on the patient's head. Two of these EEG electrodes, $A_1$ and $A_2$, are relative references, one electrode is the active or positive and the fourth electrode is the common or ground. The main EEG signal electrodes and are typically placed near the right and left ears.

As the sound input 204 is received at the sound pickup 202 and processed by the cochlear stimulation system, the EEG acquisition system 216 records the EEG signals to obtain a picture of what the residual tissue inside the cochlea looks like when it is being stimulated by a electrical current whenever sound processor processes a sound. The EEG signals are processed at the ECR waveform processor 218 by averaging the EEG signals in epochs as described above with reference to FIG. 1B. FIG. 2A shows the right and left EEG signals 218$a$ & $b$, a stimulus signal 218$c$, and a control signal 218$d$. The resulting ECR waveform information may be displayed on a user interface 220, which shows a display possible in both the time and frequency domain.

Figure 2B:
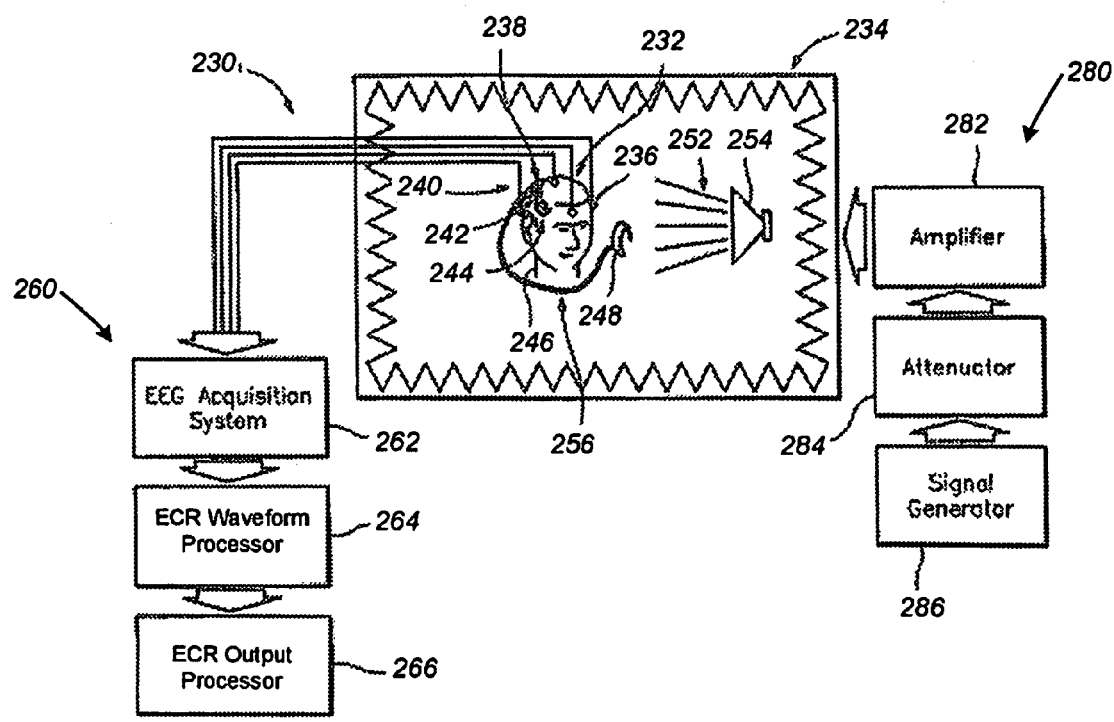
FIG. 2B is a schematic block diagram of an example system that may be used to implement the system illustrated in FIG. 2A.

FIG. 2B is a schematic block diagram of an example system that may be used to implement the system illustrated in FIG. 2A. The system 230 in FIG. 2B includes an audiometric enclosure 234 in which the patient is fitted with a cochlear stimulation system 240, an ECR detection system 260, and an input sound generator 280. The patient in the audiometric enclosure 234 is fitted with a set of EEG electrodes 232, which are used for picking up the implanted patient's EEG activity. The EEG electrodes 232 may include four EEG or "scalp" electrodes 236, for example placed on the scalp of the patient 246. The EEG electrodes 232 are connected via the scalp electrodes 236 to the ECR detection system 260.

The cochlear stimulation system 240 includes a sound processor 248 connected to a microphone worn by the patient as an earpiece via a communication link 256, an external receiver/transmitter 238, an internal receiver/transmitter 242, and an intracochlear electrode array 244. The microphone receives sound from a sound field 252 and converts the sound to electrical signals. The electrical signals are communicated to the sound processor 248 via the communication link 256. The sound processor 248 processes the electrical signals according to a selected stimulation strategy and communicates the processed signals to the external receiver/transmitter 238, which may be via a wireless link. The external receiver/transmitter 238 communicates the processed signals to the internal receiver/transmitter 242. The internal receiver/transmitter 242 is implanted in the patient's head in a location that would permit communication with the external receiver/transmitter 238. The internal receiver/transmitter 242 includes electronics for processing the signal received from the sound processor 248. The intracochlear electrode array 244 is implanted inside the patient's cochlea and connected to receive electrical signals from the internal receiver/transmitter 242. Whenever one of the intracochlear electrodes is activated, an electrical current is delivered to the patient's auditory nerve. A surface (scalp) electrical potential or voltage generated by this electrical current is picked up by the EEG electrodes 236.

The patient, who may be sedated or asleep, is positioned in the audiometric enclosure 234. The patient, while wearing cochlear stimulation system 240 is positioned near the front of an audio speaker 254, with the speaker 254 facing the microphone 248 of the cochlear stimulation system 240. The audiometric enclosure 234 is configured to be noise-free, or at least as noise-free as possible, in a sound field 252 between the speaker 254 and the microphone 248 (worn by the patient).

The ECR detection system 260 includes an EEG acquisition system 262, an ECR waveform processor 264, and an ECR output processor 266. The EEG acquisition system 262 receives EEG signals from the EEG electrodes 232 and sends the EEG signals to the ECR waveform processor 264. The ECR waveform processor 264 performs the averaging of the EEG epochs as described above with reference to FIGS. 1A-1C. The ECR waveform information may be processed by the ECR output processor 266. The ECR output processor 266 may include a user interface that provides printing and display resources to provide a clinician with a graphical representation of the measured responses, which may include ECR waveforms. The ECR output processor 266 may also include a process for automatically detecting the ECR waveforms from the measured responses and may also determine the desired information from the ECR waveforms. For example, the ECR output processor 266 may include software such as pattern recognition software to analyze the measured responses and determine which if any are ECR waveforms. The software may also determine which intracochlear electrode corresponds to the detected ECR waveforms, and determine T and C levels for the intracochlear electrode. The software may also include calibration, performance evaluation and fault detection methods, similar to the example methods described below with reference to FIGS. 3-6. The ECR output processor 266 may also include a link (not illustrated) to the cochlear stimulation system 240 to download the T and C levels directly in the cochlear stimulation system 240. Such a link may be via a wired connection, or a wireless connection.

In an example implementation, the EEG acquisition system 262 includes two channels with differential inputs operating in AC mode with a gain of 12,500 or more, a bandwidth of about 30 to 500 Hz. An A/D converter is used in an example implementation. The A/D converter may be 10 bits resolution and have two channels with a sampling rate of 20 kHz. Also in an example implementation, the ECR waveform processor 264 and ECR output processor 266 may be implemented using a general-purpose computer, or some other computerized device, that implements examples of methods described herein. In one example, the ECR waveform processor 264 may effect averaging of up to 300 epochs of EEG in intervals of up to 75 ms.

The sound stimulus for performing the fitting, calibrating, performance evaluation, etc. may be provided by the input sound generator 280. The input sound generator 280 includes a signal generator 286, an attenuator 284, and an amplifier 282. The signal generator 286 generates a signal at a selected frequency. The signal generator 286 may be programmed to generate the signal in a desired pattern, such as a random sequence of pips, or in sequences ordered in a desired way according to frequency. The programmed signal generator 286 may include a sound level input and communicate with the attenuator 284 and amplifier 282 to generate the sound at a proper $dB_{HL}$ setting.

The attenuator 284 and amplifier 282 operate to keep the signal-to-noise ratio (SNR) as low as possible, and to provide a sense of a substantially linear relation between the output sound level (in $dB_{HL}$) and the signal voltage output from the amplifier 282. The input sound generator 280 allows the clinician to control the input signal by setting a frequency and a sound intensity (in $dB_{HL}$).

In an example implementation, the input sound generator 280 is capable of generating up to 90 $dB_{HL}$ at one meter from the speaker 254 at a frequency range of 500 to 8000 Hz with a THD of less than 2%, a tolerance of 1% from the nominal frequency, and can be adjusted in increments of one, half, or third octaves.

Figure 2C:
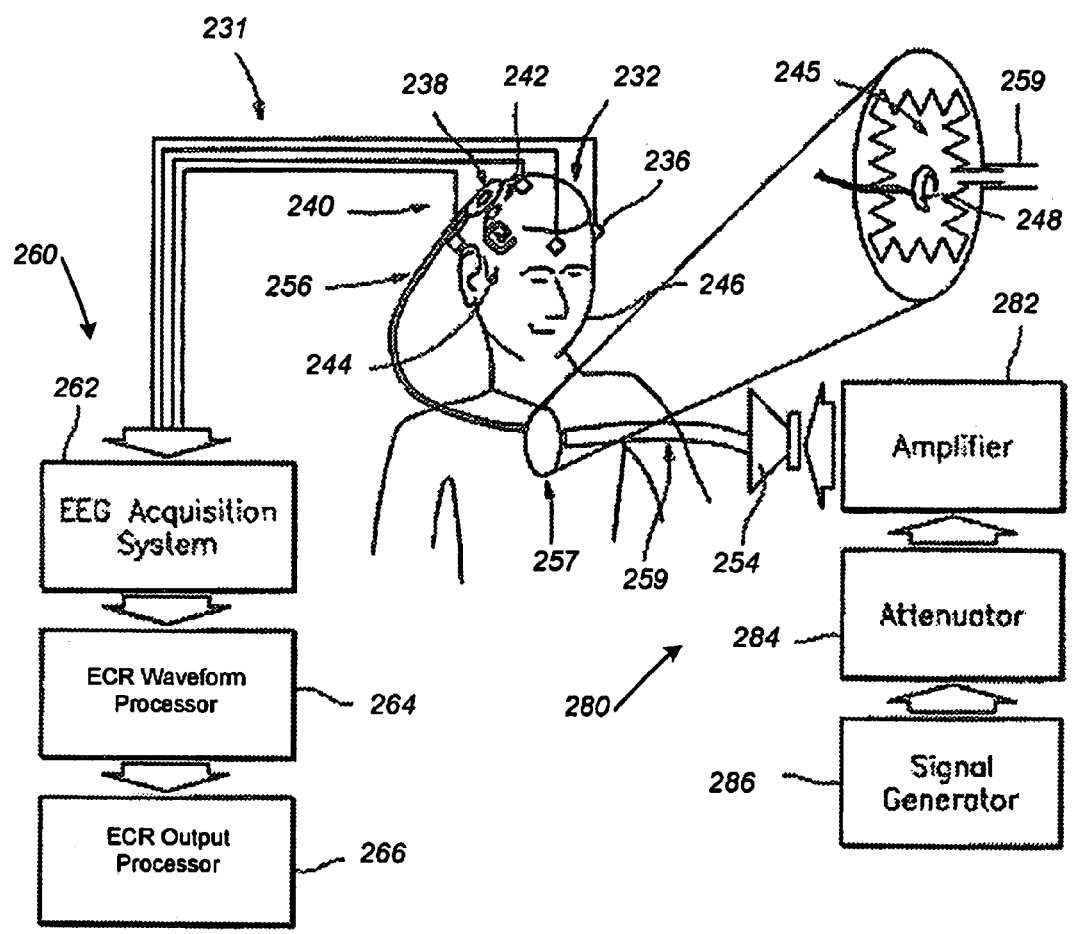
FIG. 2C is a schematic block diagram of another example system that may be used to implement the system illustrated in FIG. 2A.

FIG. 2C is a schematic block diagram of another example system that may be used to implement the system illustrated in FIG. 2A. The system 231 in FIG. 2C is similar to the system 230 in FIG. 2B including the same components. One difference between the system 200 in FIG. 2B and the system 231 in FIG. 2C includes a test sound chamber 257 of reduced dimensions. Sound from the speaker 254 is coupled to the reduced dimensions test sound chamber 257 by a waveguide 259. The sound field 245 inside the test chamber 257 is calibrated to meet the same quality requirements as in the external sound field 252 in FIG. 2B. The advantage of the reduced dimensions test chamber 257 is that it eliminates the need to perform the testing in a special room adapted to provide the desired noise-less environment. The reduced test chamber 257 provides the desired noise-less environment in a substantially portable chamber.

Figure 2D:
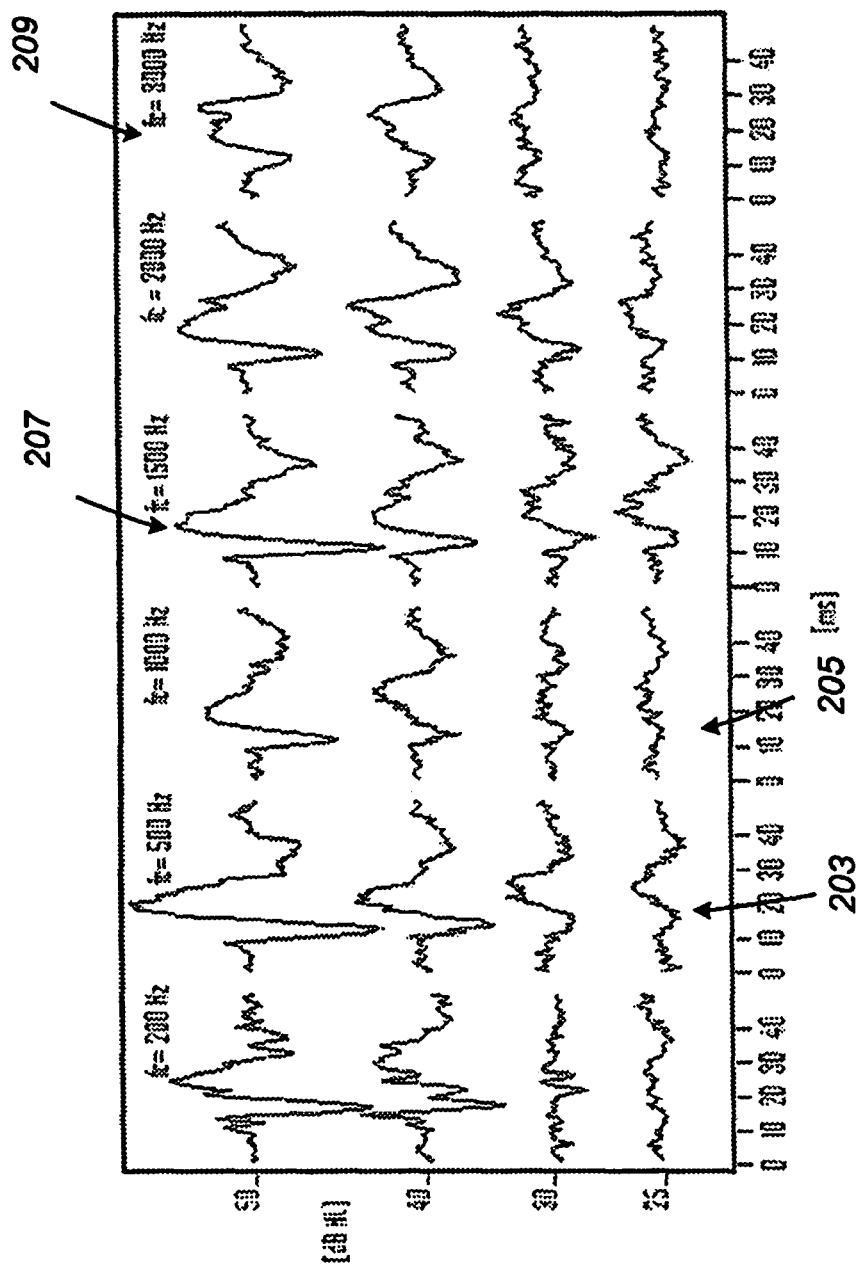
FIG. 2D is an example display that may be generated using an example of the systems illustrated in FIGS. 2A-C for analyzing operation of a cochlear stimulation system.

Once the ECR waveform processor 264 generates the ECR waveform data, it may be analyzed by a clinician either by viewing the ECR waveforms as a function of desired variables on a display, or by pattern recognition or image processing software that determines whether an ECR waveform is detected, or is becoming distorted. FIG. 2D is an example display that may be generated using an example of the systems illustrated in FIGS. 2A-C for analyzing operation of a cochlear stimulation system. The display in FIG. 2D is a series of sets of waveforms at six selected frequencies (200 Hz, 500 Hz, 1000 Hz, 1500 Hz, 2000 Hz, 3000 Hz). The sets of waveforms are plotted as a function of sound level (in $dB_{HL}$) on the vertical axis, and as a function of time on the horizontal axis. The display in FIG. 2D illustrates the progression through which the ECR waveform changes as the sound intensity is increased for each given frequency. As FIG. 2D shows, each intracochlear electrode generates ECR waveforms illustrating different behavior at the selected sound intensity levels. For example, a lowest intensity response signal 203 at 500 Hz. is beginning to display an ECR waveform as low as 25 $dB_{HL}$. A lowest intensity response signal 205 at 1000 Hz doesn't begin to show an ECR waveform. The ECR waveform at 1000 Hz doesn't begin to appear until about 40 $dB_{HL}$.

At the high intensity levels, an ECR waveform is clearly present at 50 $dB_{HL}$ for a higher intensity response signal 207 at 1500 Hz and it appears that the patient may be able to perceive the 1500 Hz sound louder than 3000 Hz sound, according to the response signal amplitudes 207 and 209. In some display outputs, the current stimulation level may also be displayed for the results.

IV. Example Methods for Fitting a Cochlear Stimulation System

Figure 3:
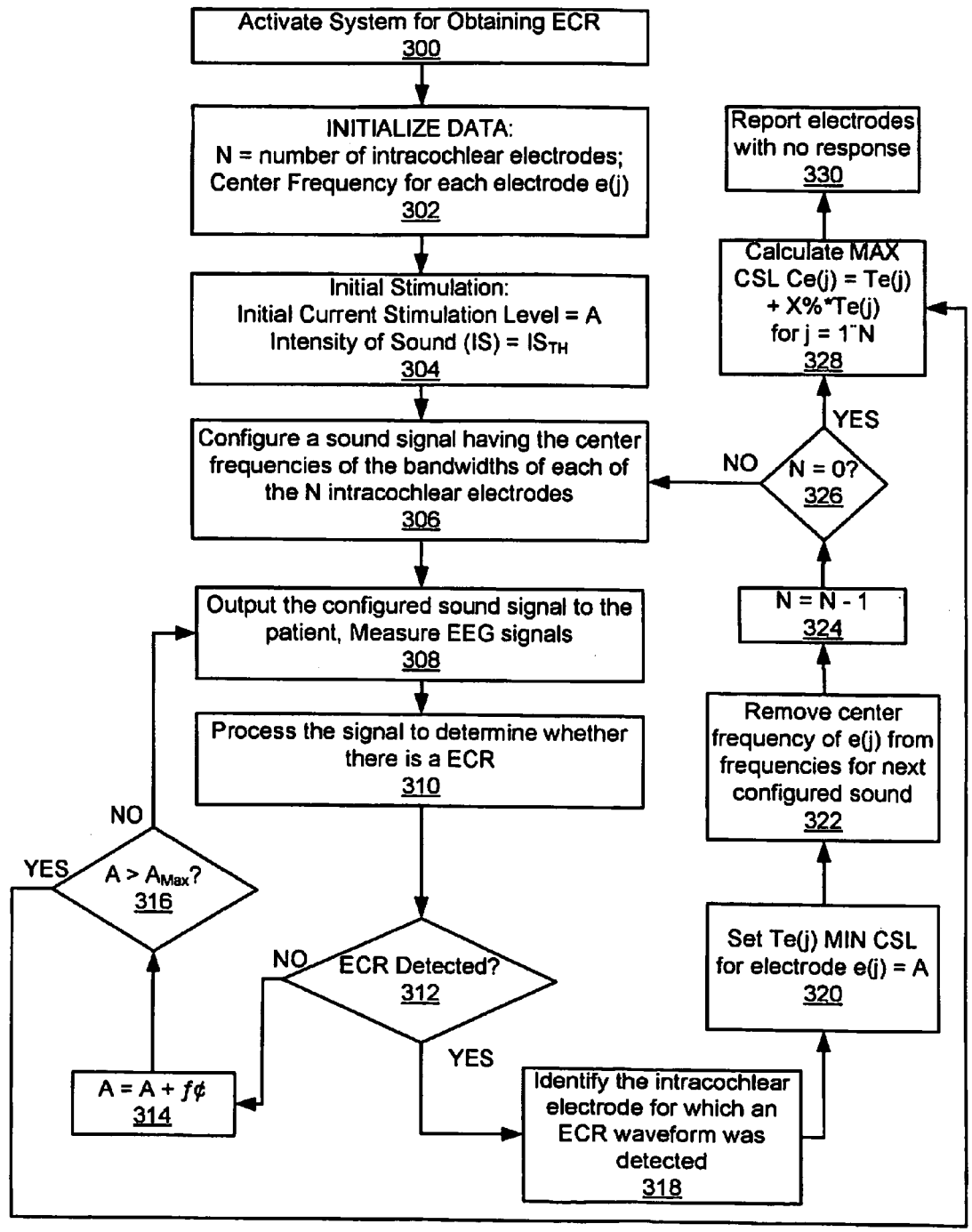
FIG. 3 is a flowchart depicting operation of an example method for fitting a cochlear stimulation system in a user.

FIG. 3 is a flowchart depicting operation of an example method for fitting a cochlear stimulation system in a user. Fitting is a procedure typically performed when a user has a cochlear stimulation system implanted. The example method described with reference to FIG. 3 is an objective method performed while the patient is sedated, or asleep, that may be performed to fit any cochlear stimulation system. The patient typically undergoes a surgical procedure to have the cochlear stimulation system implanted. The procedure involves inserting the intracochlear electrode array into the cochlea and connecting the intracochlear electrode array to the device that receives signals from the sound processor. The cochlear stimulation system is typically left in the patient for a few weeks before the fitting procedure in an unpowered state.

The fitting procedure may be performed using a system similar to the example systems for obtaining an ECR described above with reference to FIGS. 2A-2C. Once the patient is prepared for the fitting inside the audiometric enclosure 234 (FIG. 2B), or in any location if the fitting is to be performed using the reduced dimensions chamber 257 (FIG. 2C), the system for obtaining the ECR is activated (Step 300).

At step 302, the fitting method is initialized, which may involve performing any procedure necessary to enable the system to perform the fitting. As shown in FIG. 3 at step 302, the initialization at least entails identifying information about the cochlear stimulation system. This may be performed, for example, by downloading, or requesting by manual input via a user interface, information from the cochlear stimulation system's map. An example of the type of data that is used in a fitting procedure is listed in Table 1. Table 1 lists the intracochlear electrodes e(j), j=1 . . . N, N=Number of active electrodes, the frequency band assigned to the electrode, the center frequency (fc), the $T_j$ level (low threshold current stimulation level) for electrode e(j), the $C_j$ level (high threshold current stimulation level) for electrode e(j), the low threshold sound intensity $IS_{MIN}$ that correspond to T level, and the high threshold sound intensity $IS_{MAX}$ that correspond to C level. At step 302, these values may be set to initial (e.g. factory settings) values. Once the fitting procedure is complete, the T and C values will be set to values particular to the patient. At step 302, a variable N is set to the number of intracochlear electrodes and for each electrode, the center frequencies, $f_{ce(j)}$, are retrieved.

TABLE 1

| Intracochlear electrode e(j) | Frequency Band (Hz) | $f_{ce(j)}$ (Hz) | Tj (CU) | Cj (CU) | $IS_{MIN}$ ($dB_{HL}$) | $IS_{MAX}$ ($dB_{HL}$) |
|---|---|---|---|---|---|---|
| 1 | 6938-7938 | 6988 | 135 | 199 | 25 | 75 |
| 2 | 6063-6938 | 6500 | 137 | 199 | 30 | 80 |
| 3 | 5313-6063 | 5688 | 138 | 200 | 25 | 80 |
| . | | | | | | |
| . | | | | | | |
| N = 22 | 188-313 | 250 | 133 | 194 | | |

At step 304, an initial current stimulation level is set to A for each electrode. The value A should be a low current stimulation level. Current stimulation values in typical cochlear stimulation systems are between 0 and 255 Clinic Units (CU), where the lower values reflect lower current levels. Units and ranging values for measuring stimulation current may vary depending on cochlear stimulation system manufacturer. In this example, the value A should be a very low level since an objective of the fitting process is to determine a current level that permits the user to hear a desired low threshold sound level. Thus, the other parameter that is initialized in step 304 is a desired low threshold sound level, $IS_{TH}$.

At step 306, a sound stimulation signal is configured for use as the input sound signal during the fitting process. The sound stimulation signal includes center frequencies corresponding to intracochlear electrodes that are to be tested and a sound intensity. For purposes of fitting, the sound intensity is kept constant at the desired low threshold sound intensity level.

Initially, the sound stimulation signal includes a sequence of pips at each of the center frequencies of the N intracochlear electrodes. Each of the N center frequencies is generated M times. The sound stimulation signal may be configured to emit the pips in sequence as described above with reference to FIG. 1B. Each pip is to be output for a time duration, $t_d$. A pip is output in time intervals of time $t_i$, the start of which may be triggered by a control signal that may be used as a sync to the EEG acquisition system. In an example implementation, the center frequencies may be stored in an array with an initial index of N. Once the sound stimulation signal is configured, the fitting procedure continues and eventually cycles back through step 306. Each time the fitting procedure cycles through step 306, N is lower by one and a center frequency has been removed from the next configuration of the sound stimulation signal. At step 306, the remaining center frequencies are re-grouped for the next sound stimulation signal.

At step 308, the configured sound stimulation signal is output to enable the cochlear stimulation system to input the sound. As the sound stimulation signal is being output, the cochlear stimulation system is processing the sound and exciting the intracochlear electrodes corresponding to the center frequencies of each pip being generated. In addition, the patient's EEG signals are detected and recorded to determine the nervous system's response to the operation of the cochlear stimulation system. The EEG signals are input and stored for processing. In an example implementation, segments of EEG signal corresponding to the emission of individual pips are stored in groups corresponding to the frequency of the pip. The segments are stored in a memory storage having the capacity to contain the signal levels sampled at a selected sampling rate for a time equal to the analysis window, $t_{va}$ (See FIG. 1B). Each group of segments, which is referred to below as $se_{M,N}$, contains M segments such that there are M segments at each of the N center frequencies.

At step 310, the EEG signals are analyzed to determine if an ECR waveform may be detected for any of the center frequencies generated in the sound stimulation signal. In this example, the analysis involves averaging the segments at each given center frequency to generate a measured response, $SEfc_{e(j)}$, using for example, EQN. 1 according to techniques described above with reference to FIGS. 1A and 1B. The measured responses at each electrode, $SEfc_{e(j)}$, are then process to measure the ECR characteristics, such as the ECR characteristics described above with reference to FIG. 1A. For each intracochlear electrode j between 1 and N, at the given sound intensity (IS), the analysis seeks to detect, measure, and store the ECR characteristics shown in Table 2. Table 2 shows the ECR characteristics with expected values for each. It is noted that the expected values shown in Table 2 are examples of values that have been determined empirically through experimentation. The values are provided for purposes of illustration. Actual values may vary depending on the patient, equipment used and knowledge gained from continued study of ECR waveforms.

TABLE 2

| ECR Characteristic | Expected Value | Description |
|---|---|---|
| $t_A$ | <10 ms. | Maximum latency of point A |
| $t_B$ | 10 ± 2 ms. | Approximate time to Peak B |
| $t_C$ | 15 ± 2 ms. | Approximate time to Peak C |
| $t_D$ | 29 ± 2 ms. | Approximate time to Peak D |
| $Amp_{Bj}$ | $PEAKB_{MIN}$ | Minimum absolute value of Peak B amplitude |
| $Amp_{Cj}$ | $PEAKC_{MIN}$ | Minimum absolute value of Peak C amplitude |
| $Amp_{Dj}$ | $PEAKD_{MIN}$ | Minimum absolute value of Peak D amplitude |
| $|ECRj| = Amp_{Cj} - Amp_{Bj}$ | $|ECR_{MinThresh}|$ | Minimum threshold for absolute value of the difference between the Peak C amplitude and the Peak B amplitude |

At step 310, the ECR characteristics for each measured response, $SEfc_{e(j)}$, may be checked against an expected value, such as the examples shown in Table 2. A heuristic based on the expected values may be performed to determine whether a measured response is an ECR waveform. Such a heuristic is represented in FIG. 3 at decision block 312. The determination that a measured response fits the pattern of the ECR waveform signifies that the patient "hears" the tone at the center frequency, $f_{ce(j)}$, for electrode e(j) at the desired minimum threshold sound intensity level. It also signifies that the current stimulation level, A, has reached a level sufficient to fire the auditory nerve to enable the perception of hearing the tone. This may also be considered the lowest current stimulation level for the electrode e(j), which is therefore, the T level for electrode e(j).

At decision block 312, if it is determined that the measured response is an ECR waveform, at step 318 the intracochlear electrode associated with the frequency of the tone that generated the response is identified. At step 320, the map of the cochlear stimulation system is adjusted by setting the T level for e(j), Te(j), for electrode e(j) to the current stimulation level used to generate the response, which is A. At step 322, the center frequency of e(j), $f_{ce(j)}$, is removed from the set of frequencies that are to be included in the next configuration of the sound stimulation signal. At step 324, N is decremented to indicate that one less intracochlear electrode is left to be adjusted during the fitting. Decision block 326 checks to see if the last intracochlear electrode has been adjusted. If N is not 0, the next sound stimulation signal is configured at step 306. The process then continues at steps 308, 310 and decision block 312 as described above. If at decision block 326, N has reached 0, all of the intracochlear electrodes have been adjusted by having the T level set for each. At step 328, the C level for each electrode, Ce(j), may be calculated as a function of the measured T level. For example, the C level, Ce(j) may be determined as shown in step 328 using Ce(j)=Te(j)+X %*Te(j). The C level is calculated for each electrode e(j) where J=1, 2, 3, . . . , N. Once step 328 is completed, a dynamic range of the current levels used for hearing at the intracochlear electrodes has been determined.

The C level for the intracochlear electrodes may also be determined by performing the fitting procedure again, except that the initial current stimulation level, A, is initialized to be well within an estimated dynamic range, which may be determined using the equation for Ce(j) in step 328. The sound intensity level is set to a desired maximum sound intensity. A procedure containing steps similar to steps 306, 308, 310, 312, 318, 320, 322, 324, and 326 may be performed with modifications. For example, at the step similar to step 310, the measured responses are processed to determine if the ECR waveform is going away. That is, when the ECR waveform is beginning to show distortion, the sound is becoming too loud for the patient. At that point, the current stimulation level A, or a value a few levels lower may be stored as the C level for that electrode.

At step 330, intracochlear electrodes for which no response was recorded are reported to the clinician. This may be via a displayed message, or a printout, or by any suitable means for generating error reports.

Referring back to decision block 312, if no ECR waveform is detected among the measured responses, the current stimulation level, A, is incremented by a predetermined incremental value Δ. Step 314 calculates a new value of A as A=A+Δ. At decision block 316, the new current stimulation level, A, is checked against a predetermined upper limit, $A_{MAX}$. If the limit has been exceeded, the process is halted and control proceeds to step 328. If the upper limit has not been reached, the sound signal stimulation that was used in the previous cycle that resulted in the finding of no ECR waveform is re-used to see if the patient can "hear" the signal, or any part of the signal, at a higher current stimulation level.

Once the fitting process is completed successfully, the patient may use the cochlear stimulation system to hear. It is possible that after a period of continued use, the cochlear stimulation system, or the patient, may change and result in a change in the performance of the cochlear stimulation system. In such case, the ECR waveform analysis may be used to calibrate the cochlear stimulation system.

V. Example Methods for Calibrating a Cochlear Stimulation System

Figure 4:
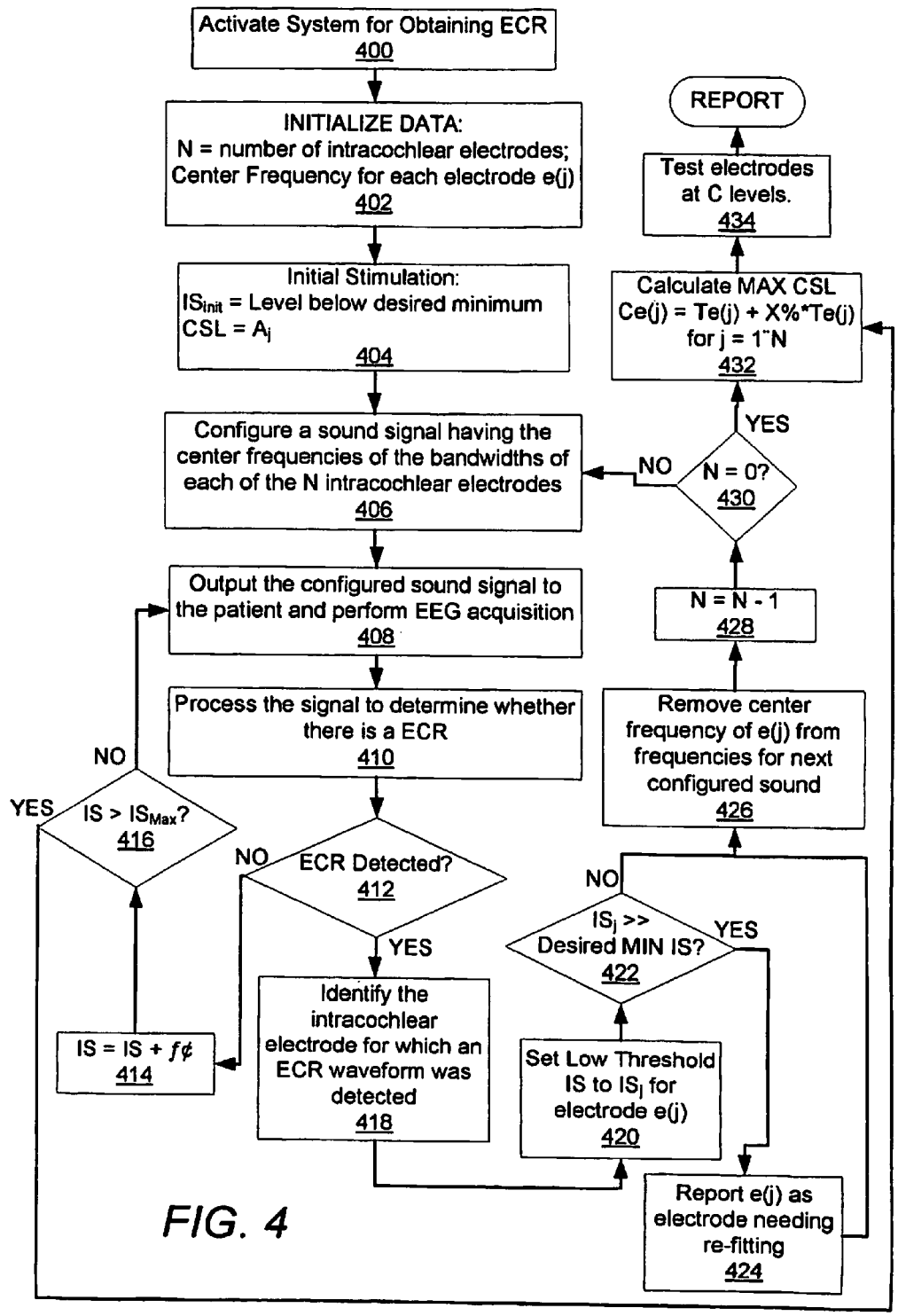
FIG. 4 is a flowchart depicting operation of an example of a method for calibrating the cochlear stimulation system.

FIG. 4 is a flowchart depicting operation of an example of a method for calibrating the cochlear stimulation system. Examples of methods for calibrating a cochlear stimulation system consistent with those described here may be used to calibrate any cochlear stimulation system.

In a calibration procedure, the patient is prepared in a manner similar to the method for fitting described above with reference to FIG. 3 using an example system for obtaining an ECR such as those described above with reference to FIGS. 2B and 2C. Once the patient is prepared for the fitting inside the audiometric enclosure 234 (FIG. 2B), or in any location if the fitting is to be performed using the reduced dimensions chamber 257 (FIG. 2C), the system for obtaining the ECR is activated (Step 400).

At step 402, the fitting method may be initialized in a manner similar to step 302 in the method for fitting in FIG. 3. According to step 402, the initialization may entail identifying the same information as in step 302 in FIG. 3. The example method of calibration in FIG. 4 is described using conventions established above in the description of the method of fitting. It is noted that one difference between the example method of fitting and the example method of calibrating is that the information retrieved in step 402 in calibrating includes MAP information that may have originated from a fitting procedure.

At step 404, the current stimulation level for each electrode is set to $A_j$, which is the current stimulation level retrieved from the cochlear stimulation system MAP. In calibration, the current settings of the MAP may be thought of as being parameters under test to determine their effectiveness in creating a perception of sound at a low sound intensity. At step 404, the sound intensity level is set to a low initial setting. During calibration, the sound intensity is increased in cycles while the current stimulation levels remain constant. In general, the initial sound intensity $IS_{init}$ should be set to a level at which one is not expected to be able to hear.

At step 406, a sound stimulation signal is configured for use as the input sound signal during the calibration process. The sound stimulation signal includes center frequencies corresponding to intracochlear electrodes that are to be tested and a sound intensity. For purposes of calibration, the sound intensity is initially as set above in step 404 and increased as the procedure is performed. The configuration of the sound stimulation signal may be performed in the same way as in step 306 in the method for fitting. In addition, step 406 proceeds with one fewer center frequency each time a cycle completes with the detection of an ECR waveform similar to step 306.

At step 408, the configured sound stimulation signal is output to enable the cochlear stimulation system to input the sound. As the sound stimulation signal is being output, the cochlear stimulation system is processing the sound and exciting the intracochlear electrodes corresponding to the center frequencies of each pip being generated. In addition, the patient's EEG signals are detected and recorded to determine the nervous system's response to the operation of the cochlear stimulation system. The EEG signals are input and stored for processing. In an example implementation, segments of EEG signal corresponding to the emission of individual pips are stored in groups corresponding to the frequency of the pip. The segments are stored in a memory storage having the capacity to contain the signal levels sampled at a selected sampling rate for a time equal to the analysis window, $t_{va}$ (See FIG. 1B). Each group of segments, which is referred to below as $se_{M,N}$, contains M segments such that there are M segments at each of the N center frequencies.

At step 410, the EEG signals are analyzed to determine if an ECR waveform may be detected for any of the center frequencies generated in the sound stimulation signal. The analysis may involve averaging the segments at each given center frequency to generate a measured response, $SEfc_{e(j)}$, as described for step 310 in the method of fitting. At decision block 412, the measured responses are processed using heuristics similar to those described above with reference to FIG. 3 at step 310.

If at decision block 412, it is determined that the measured response is an ECR waveform, the intracochlear electrode associated with the frequency of the tone that generated the response is identified at step 418. At step 420, the current sound intensity level IS is identified as the minimum sound level perceived by the patient at the intracochlear electrode e(j) determined to have responded to the stimulation signal with an ECR waveform.

At decision block 422, the measured sound intensity is compared with a sound intensity recognized as being a desirable minimum level. If the measured minimum sound intensity $IS_j$ is much greater than the desirable level, step 424 is performed. At step 424, the electrode e(j) is reported as an electrode needing to be re-fitted. Step 424 may involve identifying e(j) or marking it, and then proceeding to step 426. The actual reporting may be performed at the conclusion of the calibration method.

If at decision block 422, the difference between $IS_j$ and a desirable minimum level is not significantly greater, the center frequency, $fc_{e(j)}$, is eliminated from the center frequencies that are to be used in the next configured sound stimulation signal at step 426. At step 428, N is decremented to indicate that one less intracochlear electrode is left to be tested during the calibration. Decision block 430 checks to see if the last intracochlear electrode has been tested. If N is not 0, the next sound stimulation signal is configured at step 406. The process then continues at steps 408, 410 and decision block 412 as described above. If at decision block 430, N has reached 0, all of the intracochlear electrodes have been tested at low threshold levels.

At step 432, the C level for each electrode, Ce(j), may be calculated as a function of the measured T level. For example, the C level, Ce(j) may be determined as shown in step 432 using Ce(j)=Te(j)+X %*Te(j). The C level is calculated for each electrode e(j) where j=1, 2, 3, . . . , N. Once step 432 is completed, a dynamic range of the current levels used for hearing at the intracochlear electrodes has been determined. At step 434, the electrodes e(j) may be tested to determine if the C levels can create a perception of hearing at a sufficiently high level. The test for calibrating the cochlear stimulation system at a high sound level may be performed in a manner similar to steps 406, 408, 410, 412, 418, 420, 422, 424, 426, 428, and 430 with modifications. For example, at the step similar to step 410, the measured responses are processed to determine if the ECR waveform is going away. That is, when the ECR waveform is beginning to show distortion, the sound is becoming too loud for the patient. At that point, the sound level is compared with a desirable maximum sound level. If the sound level is significantly less than the desirable maximum, the electrode e(j) is designated as requiring re-fitting.

Referring back to decision block 412, if no ECR waveform is detected among the measured responses, the sound intensity level, IS, is incremented by a predetermined incremental value Δ. Step 414 calculates a new value of the sound intensity IS as IS=IS+Δ. At decision block 416, the new sound intensity level, IS, is checked against a predetermined upper limit, $IS_{MAX}$. If the limit has been exceeded, the process is halted and control proceeds to step 432. If the upper limit has not been reached, the sound signal stimulation that was used in the previous cycle that resulted in the finding of no ECR waveform is re-used at the higher sound intensity, IS, to see if the patient can "hear" the signal, or any part of the signal.

When the process for calibration ends, the electrodes that require re-fitting and any that did not register an ECR are reported. This may be via a displayed message, or a printout, or by any suitable means for generating error reports.

Figure 5:
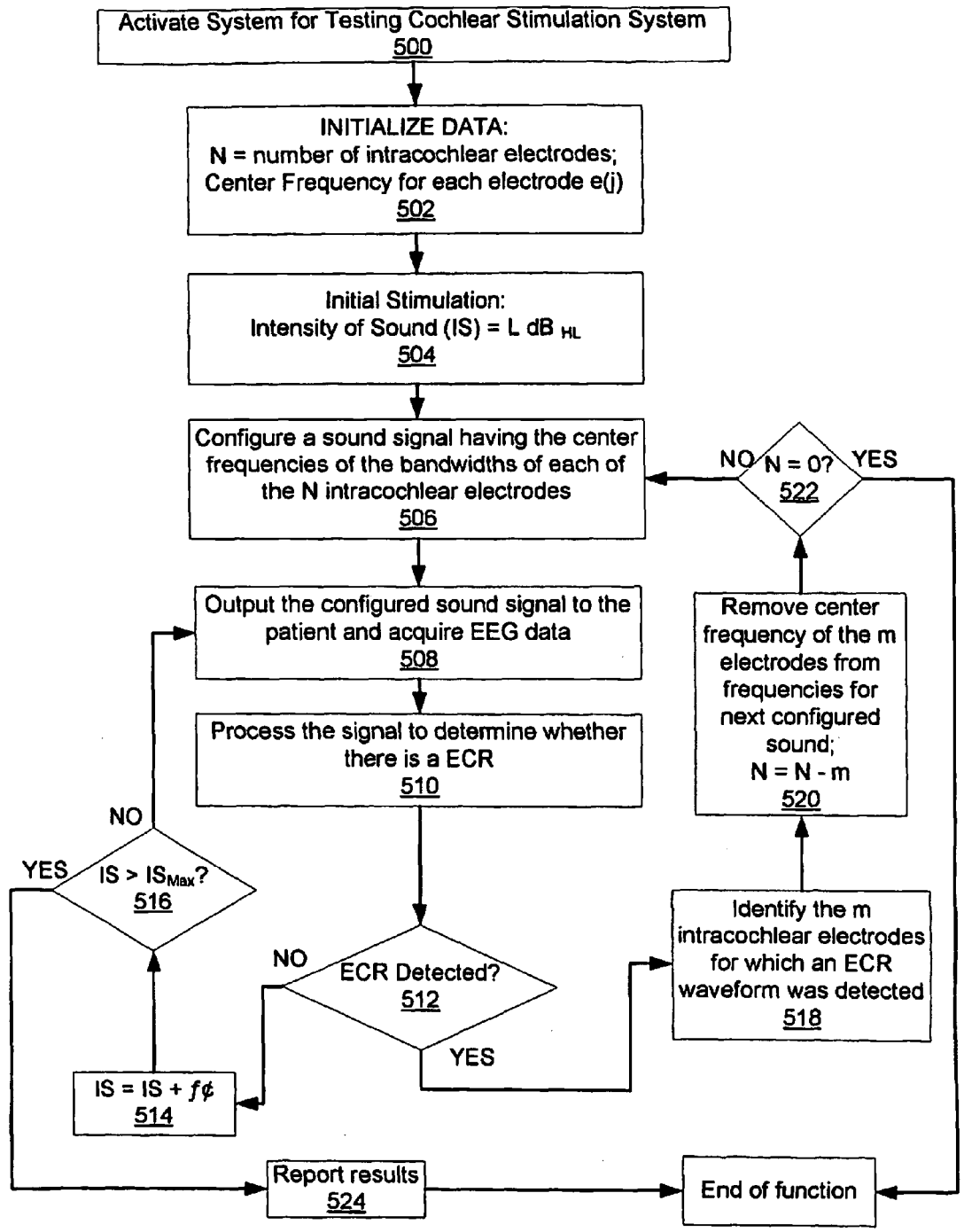
FIG. 5 is a flowchart depicting operation of an example of a method for obtaining a performance evaluation and failure detection analysis of the user's cochlear stimulation system.

VI. Example Methods for Using ECR for Evaluating Performance and Detecting Failure FIG. 5 is a flowchart depicting operation of an example of a method for obtaining a performance evaluation and failure detection analysis of the user's cochlear stimulation system. The example method illustrated in FIG. 5 provides data relating to the response of a cochlear stimulation system to sound inputs at low sound levels. The data is captured, then analyzed for indications of the performance of the cochlear stimulation system.

The example method illustrated in FIG. 5 is similar to the method shown in FIG. 4 for calibrating the cochlear stimulation system. The results of stimulating the cochlear stimulation system to produce ECR waves at a low sound intensity may be analyzed for anomalies that are indicative of a fault, or some other problem with the system.

The patient may be prepared for the method illustrated in FIG. 5 in a manner similar to the example methods of fitting and calibration described above. The system is activated at step 500. Steps 502, 504, 506, 508, 510, 512, 514, and 516 may be performed in the same manner as steps 402, 404, 406, 408, 410, 412, 414, and 416 in FIG. 4. In step 504, the initial sound intensity is set to a low level, L $dB_{HL}$. Otherwise, the description of the operation of steps 502, 504, 506, 508, 510, 512, 514, and 516 are described above with reference to FIG. 4.

At step 518, the measured responses are analyzed to detect all of the intracochlear electrodes for which an ECR was registered. All m of the N electrodes for which an ECR waveform was detected are identified. At step 520, the frequencies of the detected intracochlear electrodes are removed from the next sound stimulation signal. Decision block 522 determines if there are anymore electrodes that have not registered a response. Once all of the intracochlear electrodes have registered an ECR, or the sound intensity has exceeded a maximum, the data may be displayed in a variety of ways to determine if the cochlear stimulation system is performing properly. Examples of the types of information that may be displayed from the ECR waveform analysis include:

- ECR amplitude (|ECR|) v. Sound pressure levels in $dB_{HL}$
- ECR time latencies v. frequencies of sound stimulation
- Sufficiency of current stimulation levels in the dynamic range
- Audiometric Threshold Estimation
- Identification of intracochlear electrodes having $ECR>ECR_{MAX}$
- Identification of intracochlear electrodes that registered no ECR.

Identification of proper insertion of the intracochlear electrodes into the cochlea.

Identification of intracochlear electrodes being over-stimulated.

The data collected during the analysis, the measured responses to sound stimulation signals and detection of ECR waveforms may be displayed in different ways to determine the desired information. For example, the display shown in FIG. 2D shows a series of measured responses at each of frequencies f=200 Hz, 500 Hz, 1000 Hz, 1500 Hz, 2000 Hz, and 3000 Hz. The series of measured responses are for signals at different sound intensities from lowest to highest. The audiometric threshold at each frequency is the lowest sound intensity that generates an ECR waveform.

Figure 6A:
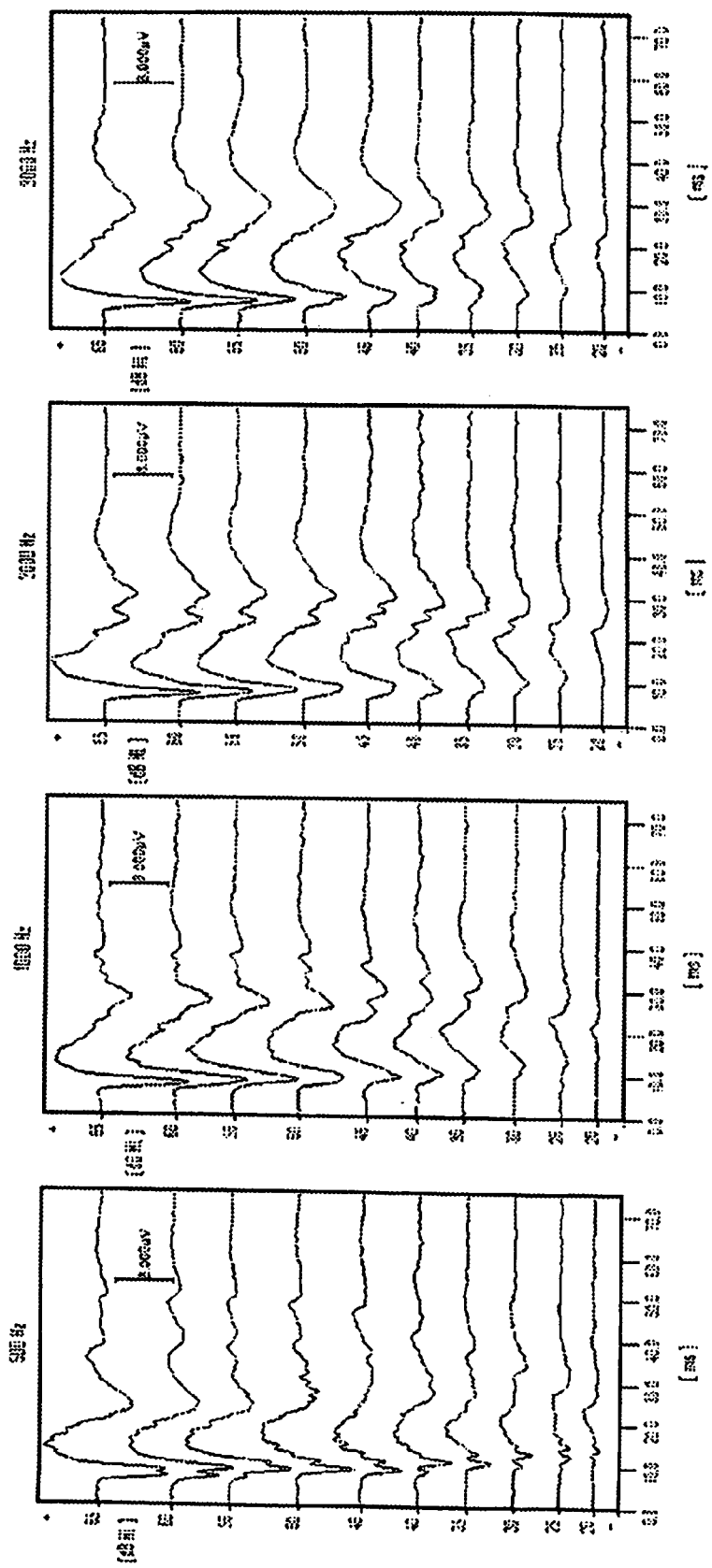
FIG. 6A is a set of graphs showing groups of ECR waveforms at selected frequencies as a function of sound intensity.

The method illustrated in FIG. 5 focuses on obtaining measured responses at low levels. In another implementation, the measured responses may be collected for a larger range of levels. For example, the measured responses may be collected for sound intensity levels through the dynamic range of sound levels corresponding to the dynamic range of the current stimulation levels of the cochlear stimulation system. The resulting measured responses may be analyzed in a variety of ways to determine how the cochlear stimulation system behaves through its dynamic range. FIG. 6A shows four series of measured response plots at frequencies f=500 Hz, 1000 Hz, 2000 Hz, and 3000 Hz. Each series of measured responses were generated by different sound intensities so that several ECR waveforms may be analyzed. The ECR waveforms may be analyzed to determine how the ECR amplitude, $|ECR_j|$, changes as the sound intensity increases. The change in time latency between Peak B and Peak C as sound intensity increases is also indicative of the cochlear stimulation system behavior. In general, the ECR amplitude, $|ECR_j|$ should increase gradually as the sound intensity increases. The time latency between Peak B and Peak C should decrease gradually as well. Too sharp an increase in ECR amplitude and too sharp a decrease in Peak B to Peak C latency may indicate overstimulation by the intracochlear electrodes, which may be corrected by calibrating the cochlear stimulation system. Too gradual an increase in ECR amplitude and to gradual a decrease in Peak B to Peak C latency may indicate understimulation.

The results shown in FIG. 6A have been determined to reflect a properly stimulated cochlear stimulation system. The results in FIG. 6A may be contrasted with those of FIG. 6B, which provides an example of an over-stimulated cochlear stimulation system.

Figure 6B:
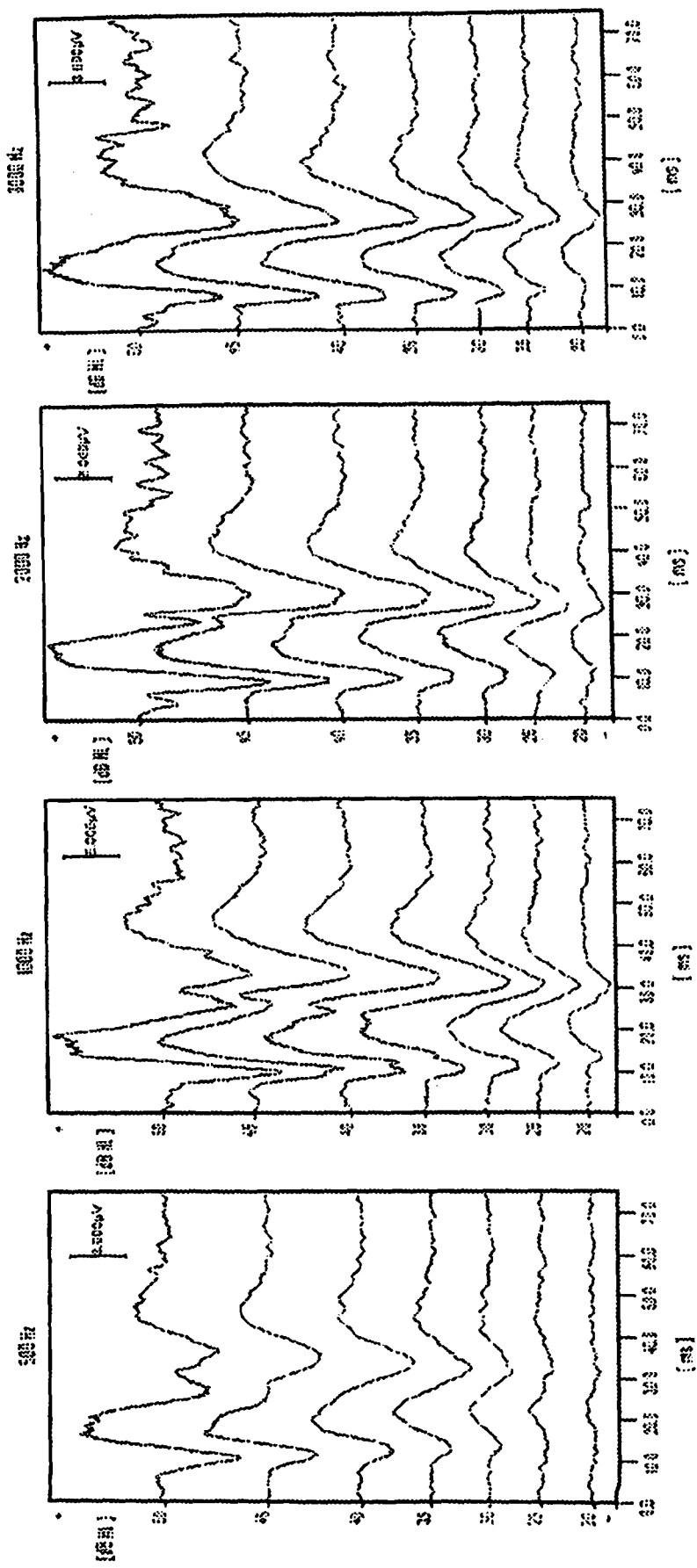
FIG. 6B is another set of graphs showing groups of ECR waveforms at selected frequencies as a function of sound intensity.

FIGS. 6A & 6B graphically display results from analyzing measured responses and displaying the results as shown. The analysis of the results leading to the conclusions indicated by the displays in FIGS. 6A & 6B may also be processed by a computer program that performs the analysis and outputs the conclusion regarding whether or not the intracochlear electrodes are over-stimulated or properly stimulated. For example, a method for detecting ECR similar to the ECR detector method described below with reference to FIG. 10A may be used to analyze measured responses in the cochlear stimulation system's dynamic range of sound intensity. A pattern recognition program, or a method similar to the ECR peak analyzer described below with reference to FIG. 10B may be used to measure peak characteristics at various sound intensities and frequencies to determine whether the cochlear stimulation system is over-stimulated.

Figure 7A:
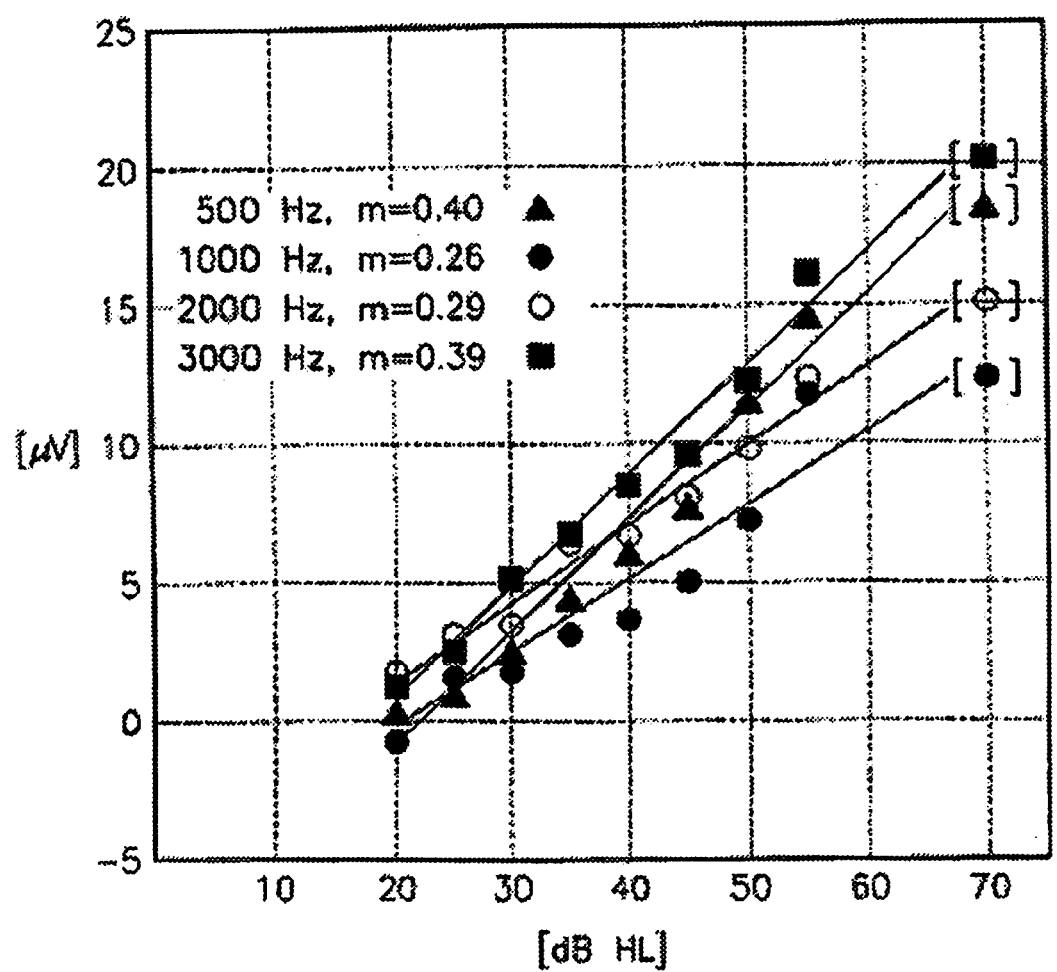
FIG. 7A is a graph of ECR amplitudes against sound intensity levels for four frequencies.

The results may be viewed in other ways. FIG. 7A is a graph of ECR amplitude growth function for four intracochlear electrodes of the implanted patient's cochlear stimulation system. The graph shows ECR amplitude, which is the Peak C and Peak B difference in amplitude, versus external intensity sound stimulation for four different frequencies f=500 Hz, 1000, Hz, 2000 Hz, and 3000 Hz. The Y-axis is the amplitude measured in micro volts ("μV"), and the X-axis is the sound levels measured in decibels ("$dB_{HL}$"). A linear regression may be performed on the amplitude showing a linear plot for frequency. The slope (m) of each line indicates the progression of the increase in ECR amplitudes with the increase of sound intensity levels. The slopes are also indicated in FIG. 7A for each frequency.

Figure 7B:
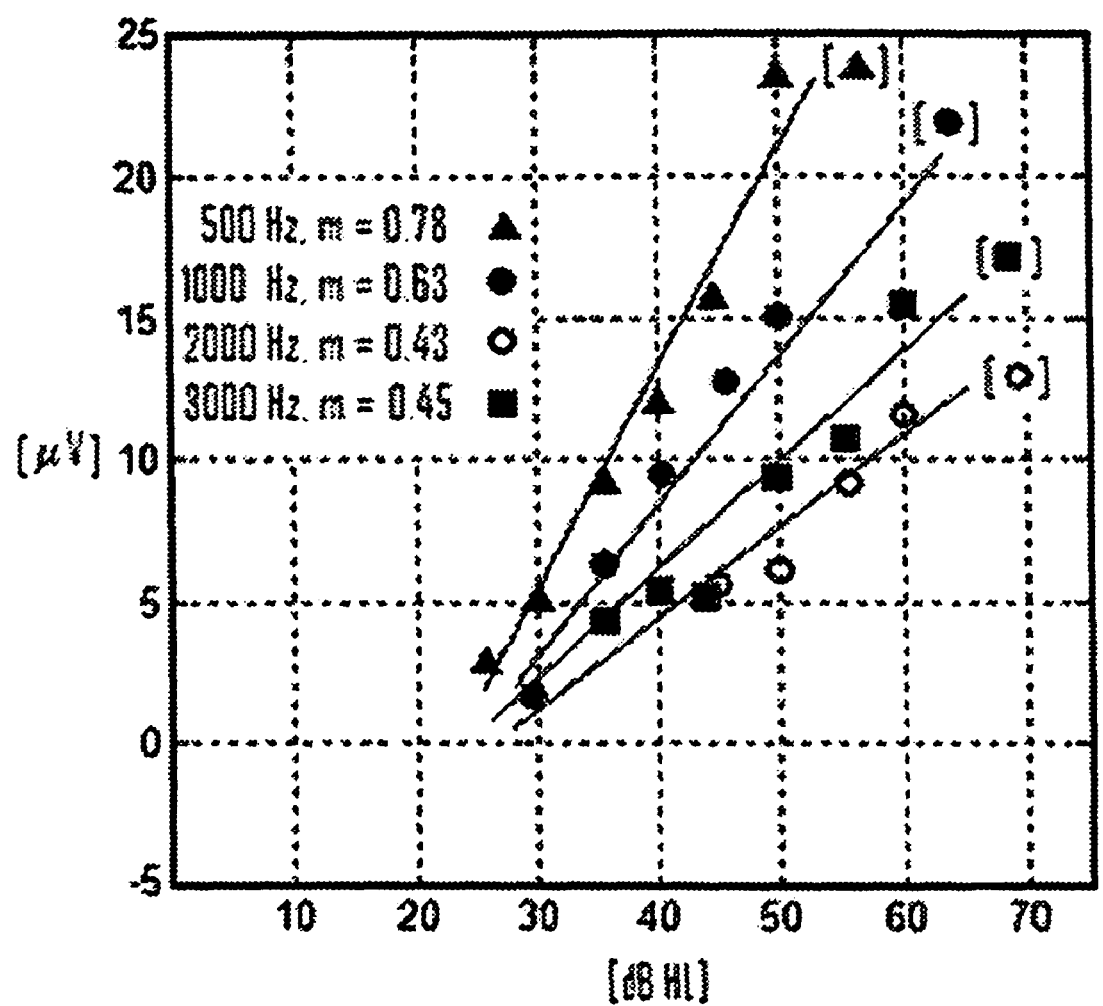
FIG. 7B is a graph of ECR amplitudes against sound intensity levels for four frequencies.

FIG. 7B shows a graph that is similar to that of FIG. 7A. Where the graph in FIG. 7A provides results for a properly stimulated cochlear stimulation system, the graph in FIG. 7B provides results for an overly stimulated cochlear stimulation system. The over-stimulation is evidenced by the higher slopes (m) of the lines in FIG. 7B.

It is noted that while the results shown in FIGS. 7A & 7B are clear in the graphical display of the data, similar results may be obtained automatically using a computer program to obtain ECR peak characteristics and compare the ECR peak characteristics to expected values. For example, data collected over time consisting of graphs such as the graph in FIG. 7A may be statistically analyzed to determine expected values for ECR characteristics and for the slopes of the lines plotted in FIGS. 7A & 7B. An ECR detector such to the ECR detector described below with reference to FIG. 10A may be used to extract measured responses indicating an ECR waveform in a collection of data taken over the dynamic range of the sound intensity for the cochlear stimulation system. An ECR waveform analyzer similar to the ECR waveform analyzer described below with reference to FIG. 10B may be used to obtain the ECR peak characteristics, and a test program may be used to analyze conclusions about the peak characteristics, and the slope of the lines plotted in FIG. 7B may be compared to expected slope values to determine whether the cochlear stimulation system is properly stimulated. Conclusions may be reached on the same basis about whether a system is being under-stimulated as well.

Figure 8:
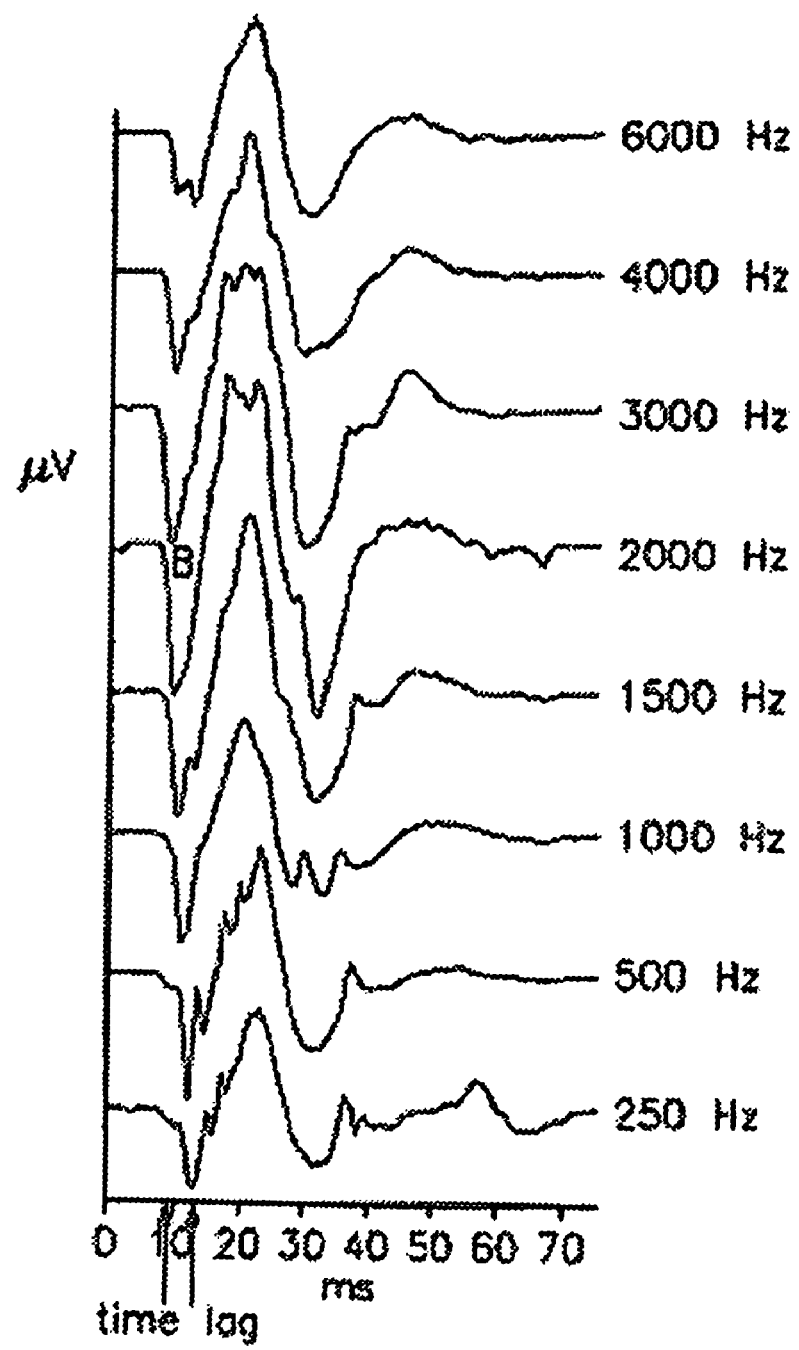
FIG. 8 is a graph showing the ECR time lag, particularly of the negative peak B, versus external sound stimulus frequency.

FIG. 8 provides another display of ECR waveforms that shows how the time latency to Peak B ($t_B$) changes with an increase in frequency. FIG. 8 depicts a series of ECR waveforms of an implanted patient for external sound stimulation of 50 dB HL at frequencies from 250 to 6,000 Hz. As shown in FIG. 8, the time latency $t_B$ increases as the frequency of the input signal is decreased. The graph in FIG. 8 reflects normal operation. The cochlea forms a spiral beginning at the oval window and ending at an apex at the conical tip of the modiolus. High frequency signals are sensed by the tissue closest to the oval window. Lower frequency sounds are processed by tissue extending progressively away from the oval window until the apex where the lowest frequencies are processed. The graph in FIG. 8 therefore reflects a properly implanted intracochlear electrode array.

Figure 9:
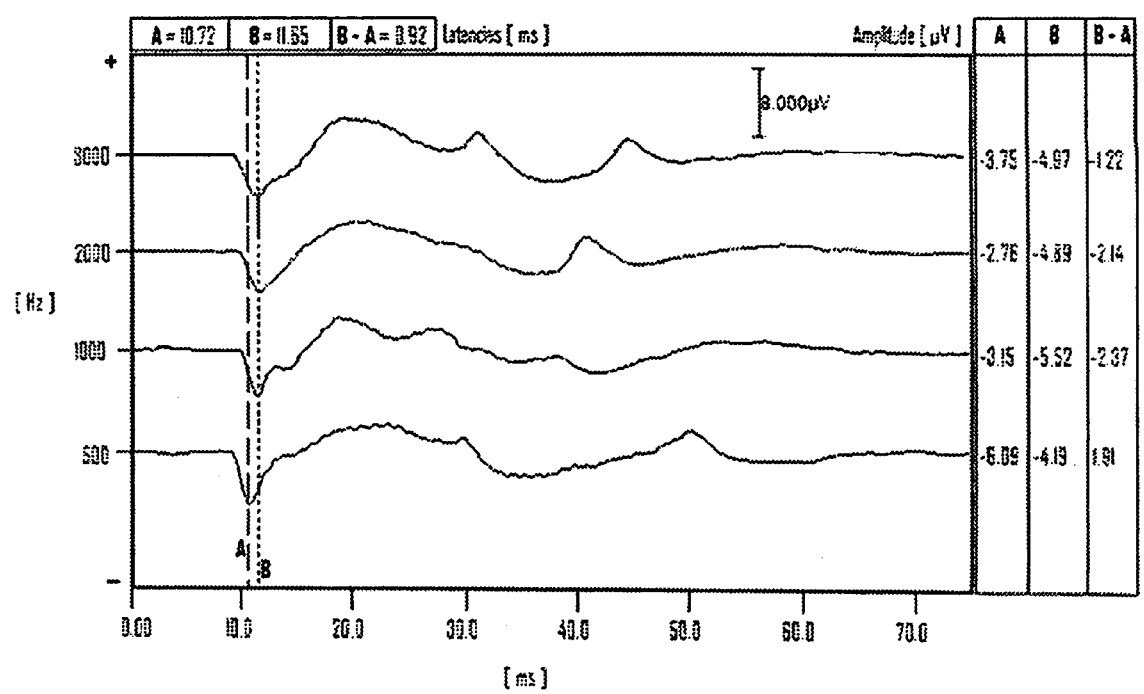
FIG. 9 is a graph illustrating the use of ECR measurement to detect an improperly implanted cochlear stimulation system in a patient.

FIG. 9 reflects another series of ECR waveforms obtained and plotted in the same manner as the graph of FIG. 8. FIG. 9 does not reflect a time latency, $t_B$, that increases as the frequency decreases. The graph in FIG. 9 reflects an improperly installed intracochlear electrode array.

It is noted that while the results displayed in the graphs in FIGS. 8 and 9 are output to a display for analysis. A computer program may also be used to process the data from measured responses to arrive at the same conclusions. An ECR waveform analyzer similar to the method described below with reference to FIG. 10B may be used to process the measured responses through the entire sound dynamic range of the cochlear stimulation system. The time latency at $t_B$ may be compared across the frequency range used to obtain the measured responses and insure that the time latency increases as the frequency is lower, which is as expected.

VII. Automated ECR Waveform Analysis

Figure 10A:
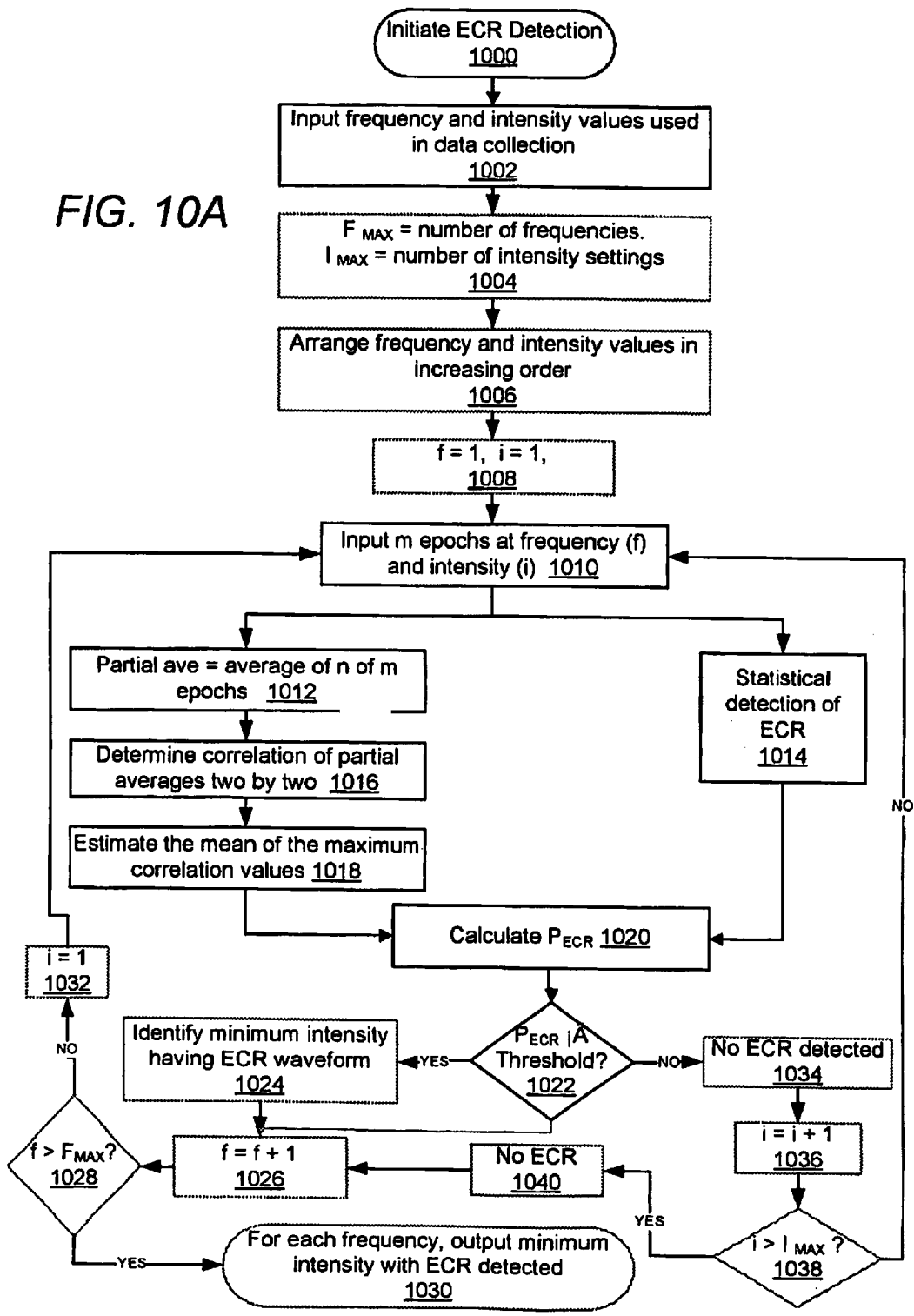
FIGS. 10A-10B are flowcharts depicting operation of a method for analyzing a collection of EEG signal epochs to detect ECR waveforms.
Figure 10B:
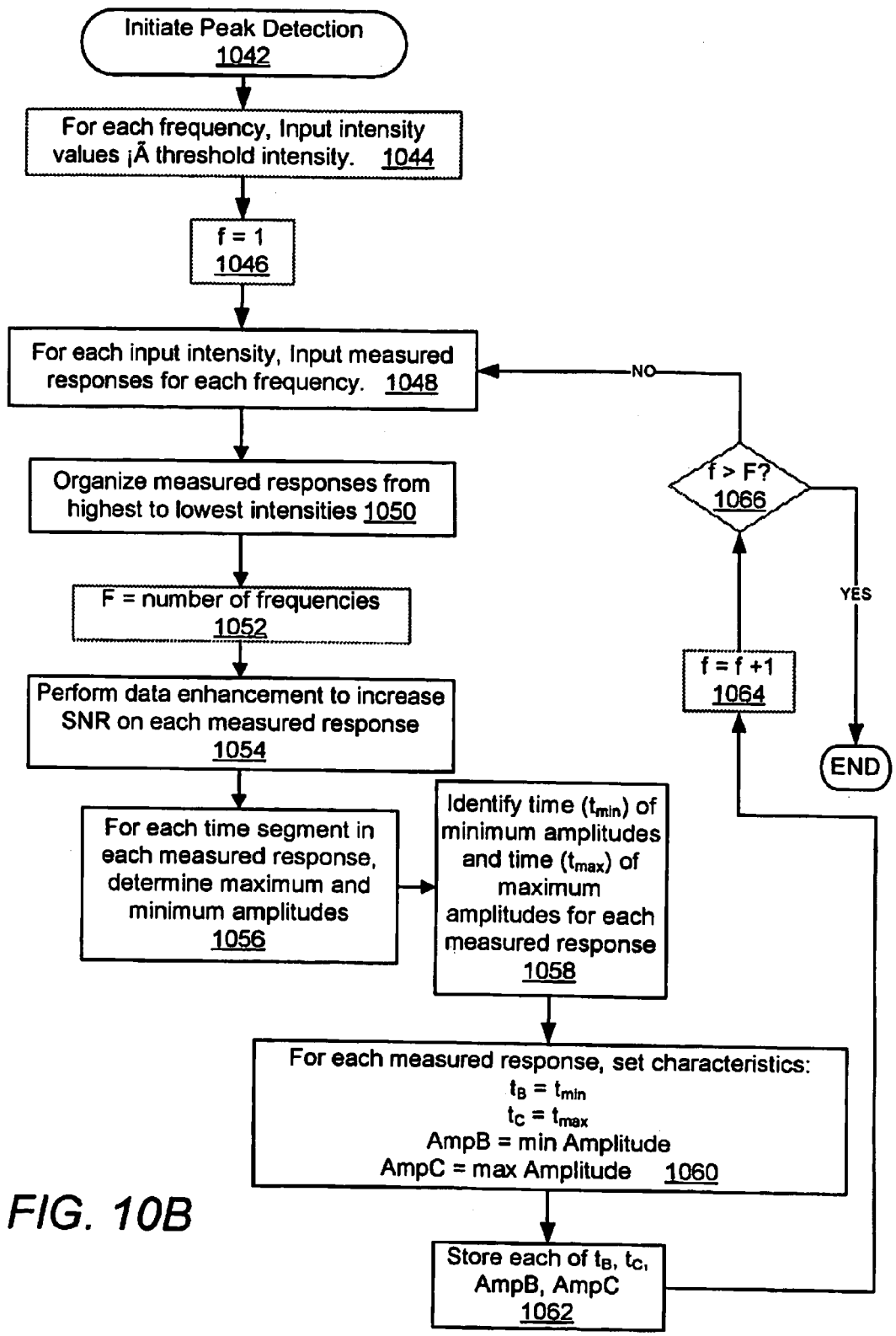

FIGS. 10A-10B are flowcharts depicting operation of a method for analyzing a collection of EEG signal epochs to detect ECR waveforms. The methods illustrated in the flowcharts in FIGS. 10A and 10B provide automated ECR waveform analysis and may be configured to automate processes of fitting, calibration, performance evaluation, fault detection, or any other procedure relating to operation of the cochlear stimulation system. The methods may be implemented in any computer-controlled device configured to receive data obtained from measuring a patient's electrical responses to operation of an implanted cochlear stimulation system in a sound field created by a sound stimulus signal. The examples illustrated by FIGS. 10A and 10B are described in the context of data collected using examples of systems described above with reference to FIGS. 2A-2C. However, the data may be obtained using any system or method for any cochlear stimulation system. The systems described above with reference to FIGS. 2A-2C may be provided with hardware and software as an ECR detector to perform examples of methods described in FIG. 10A, and as an ECR peak analyzer to perform methods described in FIG. 10B.

Referring to FIG. 10A, a method for detecting ECR waveforms is initiated at step 1000 when a desired collection of data is available. The collection of data includes data sufficient for a desired objective. For example, in a fitting, the collection of data may include data representing responses at all frequencies of operation of the cochlear stimulation system and all intensities within a maximum desired dynamic range of sound intensities. In a performance evaluation, the collection of data may be more limited. For example, in audiometric threshold estimation, only a lower range of sound intensities may be needed.

The system used to perform the example methods illustrated in FIGS. 10A and 10B may be integrated with a computer-controlled device designed to carry out any combination of the functions performed by the components in the ECR detection system 260 in FIGS. 2B and 2C in some example implementations. In such cases, step 1002 may be performed as an integrated data input step in an automated system for fitting and analyzing cochlear stimulation systems. In other examples, the methods illustrated in FIGS. 10A and 10B may be performed on a general-purpose computing platform, which may receive the collected data by download, or by reading from a data-storage medium, such as a CD, tape, portable storage drive, or any other suitable medium.

At step 1002, the frequencies and intensities used in the sound stimulus signal generated in collecting the data are input or identified. The frequencies and intensities used may be obtained from the response data collected. At step 1004, the frequencies and intensities input in step 1002 are counted to determine the total number of each as $I_{max}$=total number of intensity values input, and $F_{max}$=total number of frequency values. At step 1006, the frequency values and intensity values are ordered from minimum to maximum. At step 1008, indices are initialized for the collections of frequency and intensity values. An index f is initialized to f=1 to address the first frequency value in the collection of frequencies. An index i is initialized to i=1 to address the first intensity value in the collection of intensities.

At step 1010, a collection of m epochs at frequency F(f) and intensity I(i) are input from the response data. At step 1012, the epochs are organized in k groups of n epochs such that k=m/n. A partial average $P_A$ is calculated by averaging the epochs in each group k of the m epochs: $P_A$=Average of n epochs in group A, for each A=1, . . . m/n. The values of m, n, and k are preferably even numbers.

At step 1014, a parallel analysis may be performed on the same set of data. In an example implementation, a known statistical processing method such as, for example, the Fisher Single Point (FSP) method, may be used to analyze the collection of m epochs at frequency F(f) and intensity I(i). The selected method may set a variable $D_E$ to indicate either true (T) or false (F) in relation to whether or not an ECR waveform is detected.

At step 1016, a correlation, $R_{xy}(P_A, P_{A+1})$, is calculated of the partial average of each consecutive pair of groups of k epochs, $P_A$ and $P_{A+1}$. At step 1018, the resulting set of correlation values is analyzed to determine a mean of the correlation values greater than a selected upper threshold correlation value for the k partial averages, $P_A$.

At step 1020, a probability, $P_{ECR}$, that the m epochs are an ECR waveform is calculated based on the correlation values, $R_{xy}$, and on the variable $D_E$. At decision block 1022, the probability, $P_{ECR}$, is compared to a threshold probability. If probability, $P_{ECR}$, is greater than or equal to the threshold probability, an ECR waveform is detected in the epochs collected for frequency f and intensity i. The process continues at step 1024 for identification of the intensity i as the minimum sound intensity for which an ECR waveform is detected at frequency f. The frequency f and intensity i are stored with an indication of detection of ECR for the corresponding EEG epochs. At step 1026, the next frequency is selected by setting index f=f+1. At decision block 1028, the index f is checked to determine if the last frequency in the group of frequencies has been analyzed. If f is not greater than $F_{Max}$, the index i is reset back to the first intensity (i=1) of the group of intensities at step 1032. The process then continues at step 1010. If the last frequency has been analyzed, the results are reported for each frequency at which an ECR was detected at step 1030.

Referring back to decision block 1022, if the probability of ECR, $P_{ECR}$, is less than the threshold, the non-detection of an ECR waveform is indicated at step 1034. At step 1036, the intensity index i is incremented to analyze epochs collected at the next intensity. At decision block 1038, the index i is checked to determine if the last of the intensities (I(i)>$I_{MAX}$) has been reached. If I(i)>$I_{MAX}$, step 1040 is processed to indicate that no ECR waveform was detected for the frequency f, and step 1026 is performed to continue processing at the next frequency. If at decision block 1038, I(i)≤$I_{MAX}$, the m epochs for the new intensity value at i and frequency f are analyzed for an ECR waveform at step 1010.

The example method illustrated in FIG. 10A may be performed to detect ECR waveforms at low thresholds of intensity, and may be sufficient for performing fitting, calibration, audiometric threshold estimation, or other functions in which the low threshold of intensity at selected frequencies, is of interest. The results may be reported on a display, printer, or stored for use by another function, such as for example, a function for automatically setting the dynamic range of the cochlear stimulation system based on the ECR detection.

FIG. 10B illustrates an example of a method for analyzing ECR peaks and latencies to provide information regarding the performance or to detect faults in the cochlear stimulation system. The example method in FIG. 10B is initiated at step 1042 after performing an example of the method in FIG. 10A. The method in FIG. 10B processes data collected for a wider range of sound intensities. At step 1044, the data corresponding to the frequencies and minimum intensities is collected. In addition, for each frequency, data corresponding to intensities greater than the minimum intensity is also collected. At step 1046, a frequency index, f, is initialized to f=1 to input the averages of the EEG epochs where the first element is the frequency at f=1 at which an ECR waveform was first detected. At step 1048, a collection is made of the averages of the EEG epochs corresponding to the minimum sound intensity at which an ECR waveform is detected, or greater, for the frequency f. At step 1050, the averages of EEG epochs at frequency f are organized by descending intensity.

At step 1052, the number of frequencies at which an ECR waveform is detected is counted. At step 1054, a data enhancement technique is performed on the ECR waveform to improve the SNR. Such a data enhancement technique may include curve fitting or smoothing techniques, or other techniques, that may interpolate the data. At step 1056, the maximum and minimum values within each measured response (averaged epochs within a time segment, e.g. analysis window) at each sound intensity value are determined and stored. At step 1058, the times $t_{min}$ and $t_{max}$ are determined. The time $t_{min}$ is the time latency of Peak B, which is the time at which the minimum amplitude, Peak B, is reached. The time $t_{max}$ is the time latency of Peak C, which is the time at which the maximum amplitude, Peak C, is reached. At step 1060, the ECR characteristic parameters $t_B$, $t_C$, AmpB and AmpC are set as follows:

$t_B = t_{min}$
$t_C = t_{max}$
AmpB=min Amplitude
AmpC=max Amplitude

At step 1062, the ECR characteristic parameters, $t_B$, $t_C$, AmpB and AmpC, are stored as characteristics for the ECR waveform detected at the given frequency f and for each intensity i. At step 1064, the data for the next frequency is analyzed by setting the index f=f+1. Decision block 1066 checks the index f to determine if it is greater than the total number of frequencies, F. If it is, then processing ends. If it is not, the next frequency is analyzed, starting at step 1048.

While the present invention has been described with reference to certain embodiments, it will be understood by those skilled in the art that various changes can be made without departing from the scope of the present invention. It will be understood that the foregoing description of an implementation has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

We claim:

1. A system for analyzing operation of a cochlear stimulation system implanted in a patient, the system comprising:
   a sound generating system for generating a sound stimulus signal to elicit operation of the cochlear stimulation system;
   an electrical cochlear response ("ECR") detection system to detect an ECR waveform in a plurality of electro encephalographic (EEG) signals received from the patient using surface electrodes, the EEG signals being generated in response to the sound stimulus signal; and
   an ECR waveform processor configured to receive the EEG signals and to process the EEG signals to generate measured responses at selected frequencies and sound intensities, the ECR waveform processor being configured to facilitate analysis of the measured responses to detect ECR waveforms in the measured responses, the ECR waveform being indicative of operation of the cochlear stimulation system.

2. The system of claim 1 where the ECR detection system comprises:
   an electro encephalographic (EEG) acquisition system for detecting the EEG signals generated by the patient's nervous system in response to the processing of the sound stimulus signal by the cochlear stimulation system.

3. The system of claim 1 where the sound generating system includes:
   a signal generator for configuring the sound stimulation signal according to a given set of frequencies;
   an amplifier for amplifying the stimulation signals to generate the sound stimulation signal at a given sound pressure level; and
   an electroacoustic transducer coupled to the amplifier for creating a sound field in proximity to a sound input of the cochlear stimulation system.

4. The system of claim 3 where the signal generator configures the sound stimulation signal as a sound pattern of m pips at each of N frequencies in a selected frequency range, each pip being generated in sequence for a time duration $t_d$, each pip being separated by a time interval $t_i$.

5. The system of claim 2 where the EEG acquisition system includes a plurality of EEG electrodes placed on the patient at locations selected for detecting EEG signals in response to the sound stimulus signal.

6. The system of claim 2 where the ECR waveform processor includes:
   hardware and software configured to receive the EEG activity in EEG epochs having a length of time equal to an analysis window, $t_{wa}$, sufficient to include the time duration, $t_d$, of each pip, and to collect the EEG epochs according to the sound intensity level and frequency of the sound signal; and
   an ECR waveform processor to generate measured responses to the sound stimulus signal at selected sound intensities and frequencies.

7. The system of claim 1 further comprising an audiometric enclosure in which the patient is subject to testing.

8. The system of claim 1 further comprising a reduced dimension test sound chamber in which the electroacoustic transducer is mechanically coupled to a microphone of the cochlear stimulation system.

9. The system of claim 2 further comprising:
   an ECR detector to automatically analyze measured responses to determine if a given measured response includes an ECR waveform to facilitate detection of the ECR waveform.

10. The system of claim 9 further comprising:
    an ECR peak analyzer configured to detect ECR characteristics in measured responses.

11. The system of claim 2 further comprising:
    a user interface including a display; and
    a graph analysis system for configuring the display of measured responses in a manner that would facilitate detection of the ECR waveform.

12. A method for analyzing operation of a cochlear stimulation system implanted in a patient, the method comprising:
    generating a sound stimulus signal having at least one selected frequency and sound intensity;
    detecting a plurality of EEG signals generated in response to the sound stimulus signal;
    processing the EEG signals as measured responses to the sound stimulus signal at generated frequencies and sound intensities; and
    analyzing the measured responses to determine if the electrical signal responses include an electrical cochlear response ("ECR") waveform, the ECR waveform being indicative of operation of the cochlear stimulation system.

13. The method of claim 12 where the step of detecting the plurality of EEG signals further comprises:
inputting EEG signals from the patient using an EEG acquisition system.

14. The method of claim 13 where the step of processing the EEG signals includes:
averaging the EEG signals corresponding to the sound stimulus signal at a given frequency and sound intensity organized as EEG signal epochs, the averaged EEG signal epochs being the measured response at the given frequency and sound intensity.

15. The method of claim 12 further comprising:
adjusting a setting of a current stimulation level on the cochlear stimulation system to a low starting level;
generating the sound stimulus signal at a desired minimum threshold hearing intensity level;
performing the steps of processing, detecting and analyzing the measured responses for a given frequency, desired minimum threshold hearing intensity level and given current stimulation level;
if the ECR waveform was not detected, adjusting the current stimulation level by increasing by a selected incremental level and repeating the steps of generating the sound stimulus signal and of performing the steps of processing, detecting, and analyzing; and
if the ECR waveform was detected, identifying an intracochlear electrode corresponding to the given frequency of the measured response and setting a minimum current stimulation level for the identified intracochlear electrode to the given current stimulation level setting.

16. The method of claim 15 further comprising:
fitting the cochlear stimulation system by repeating the steps of claim 15 until a minimum current stimulation level is identified for each intracochlear electrode.

17. The method of claim 16 further comprising:
setting a maximum current stimulation level for each intracochlear electrode by calculating:

Maximum Current Stimulation Level=Minimum Current Stimulation Level+x %*Minimum Current Stimulation Level.

18. The method of claim 12 further comprising:
identifying the frequency and minimum intensity of the sound stimulus signal that elicited electrical responses forming the ECR waveform for each frequency corresponding to each intracochlear electrode in the cochlear stimulation system;
at each frequency, comparing the minimum intensity to a desirable minimum threshold sound intensity; and
performing a fitting of the cochlear stimulation system if the minimum intensity is significantly greater than the desirable minimum threshold sound intensity.

19. The method of claim 12 further comprising:
identifying the frequency and minimum intensity of the sound stimulus signal that elicited electrical responses forming the ECR waveform for each frequency corresponding to each intracochlear electrode in the cochlear stimulation system; and
reporting an audiometric threshold for each frequency by indicating the identified minimum intensity for each frequency.

20. The method of claim 12 where the at least one sound intensity includes a selected range of sound intensities and the at least one frequency includes a selected range of frequencies, the method further comprising:
performing the steps of processing, detecting and analyzing the measured responses for each frequency in the selected frequency range and for each sound intensity in the selected sound intensity range;
analyze the ECR waveforms detected in the analyzing step to analyze performance and detect faults in the cochlear stimulation system.

* * * * *